United States Patent
Ramharack et al.

(10) Patent No.: US 6,607,893 B2
(45) Date of Patent: Aug. 19, 2003

(54) DIACYLGLYCEROL ACYLTRANSFERASE (DGAT) ASSAY

(75) Inventors: Randy Ranjee Ramharack, Ann Arbor, MI (US); Mark Allan Spahr, Ann Arbor, MI (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 10/027,938

(22) Filed: Dec. 19, 2001

(65) Prior Publication Data

US 2002/0127627 A1 Sep. 12, 2002

Related U.S. Application Data

(60) Provisional application No. 60/258,681, filed on Dec. 28, 2000.

(51) Int. Cl.$^7$ .............................. C12Q 1/48; C12Q 1/00
(52) U.S. Cl. ................... 435/15; 435/4; 435/19
(58) Field of Search ................. 435/15, 4, 19

(56) References Cited

U.S. PATENT DOCUMENTS

2002/0127627 A1 * 9/2002 Ramharack et al. .......... 435/16

OTHER PUBLICATIONS

Gaziano J., Hennekens C., O'Donnell C., Breslow J., Buring J., Fasting triglycerides, high–density lipoprotein, and risk of myocardial infarction. Circulation 1997; 96: 2520–2525.

Coleman R., Bell R., Triacylglycerol synthesis in isolated fat cells, J. Biol. Chem. 1976: 251: 4537–4543.

Bostrom K., Boren J., Wettesten M., et al., Studies on the assembly of apo B–100–containing lipoproteins in HepG2 cells, J. Bio. Chem., 1988; 263: 4434–4442.

Pullinger C., North J., Teng B., Rifici V., Ronhild de Brito A; Scott J., The apoliopoprotein B gene is constituitively expressed in HepG2 cells: regulation of secretion by oleic aid, albumin, and insulin, and measurement of the mRNA half–life, J. Lipid Res., 1989; 30: 1065–1077.

Coleman R., Diacylglycerol acyltransferase and monoacylglycerolacyltransferase from liver and intestine, Methods in Enzymology, 1992; 209: 98–204.

Lehner R, Kuksis A., Biosynthesis of triacylglycerols, Prog. Lipid Res., 1996; 35 (No. 2): 169–201.

Bell R., Enzymes of glycerolipid synthesis in eukaryotes, Ann Rev. Biochem, 1980; 49: 459–487.

\* cited by examiner

*Primary Examiner*—Louise N. Leary
(74) *Attorney, Agent, or Firm*—David R. Kurlandsky

(57) ABSTRACT

The present invention provides a method for measuring diacylglycerol acetyltransferase (DGAT) activity which utilizes a novel solvent system to reduce and/or eliminate the activities of related compounds.

The present invention also discloses a method for determining whether a compound is useful for modulating DGAT biological activity. The method is capable of being utilized for mass screening of compounds as modulators of the biological activity of DGAT.

48 Claims, 18 Drawing Sheets

Effect of Ethanol on Microsomal Enzyme Activities

Assays related to Figures 1 A-E were performed at 37 °C for 5 minutes using 4 μg of microsomal protein (ethanol, chloroform, ethanol:chloroform) or 1.25 μg of microsomal protein (acetone, acetone:chloroform), 3.33 nCi of [$^{14}$C]Oleoyl CoA, 403 μM of 1,2-dioleoyl-sn-glycerol, ethanol, acetone, and chloroform at the indicated concentration for each reaction. N-(7,10-dimethyl-1,1-oxo-10,11-dihydro-dibenzo[b,f][1,4]oxazepin-2-yl)-4-hydroxy-benzamide was made up in DMSO to 100x and diluted to final indicated concentrations. Values represent averages, n=3 ± SEM.

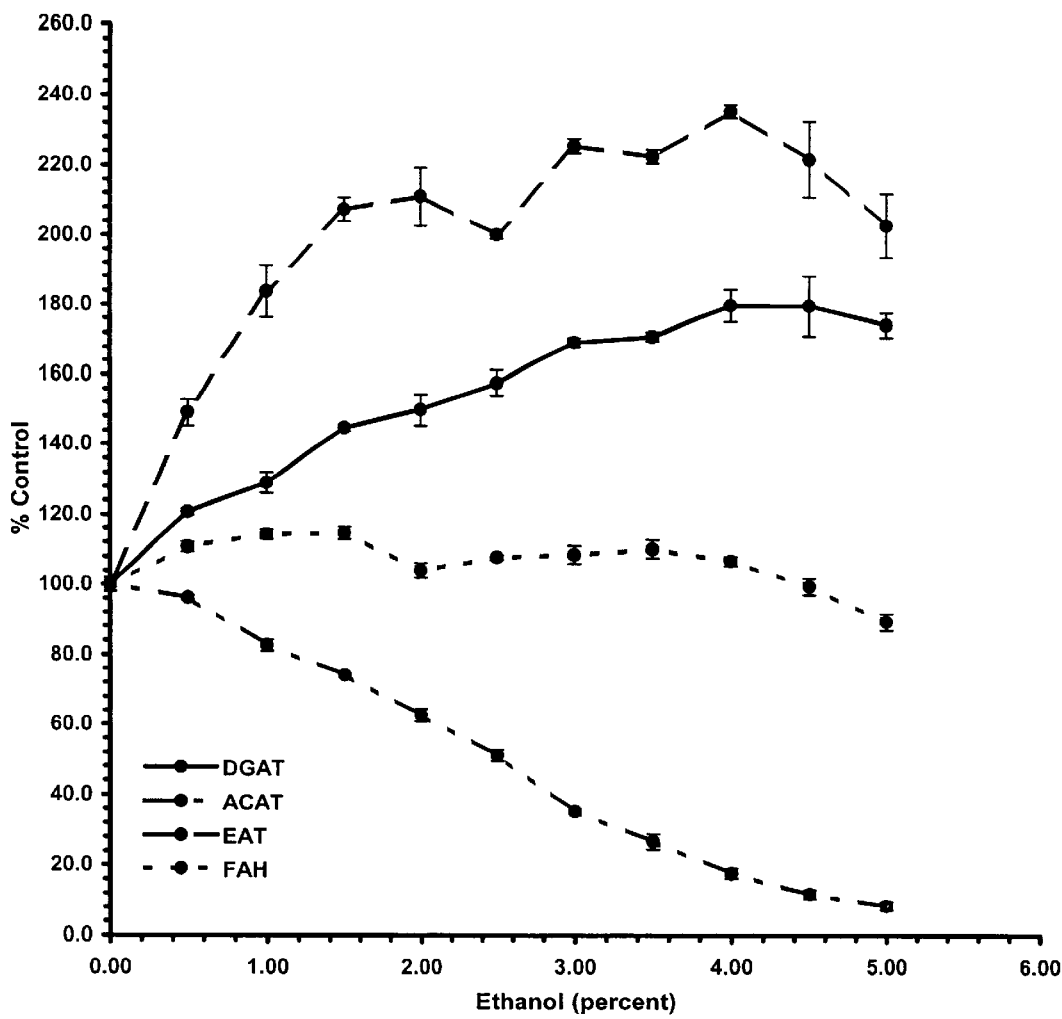

Figure 1A. Effect of Ethanol on Microsomal Enzyme Activities

Assays related to Figures 1 A-E were performed at 37 °C for 5 minutes using 4 µg of microsomal protein (ethanol, chloroform, ethanol:chloroform) or 1.25 µg of microsomal protein (acetone, acetone:chloroform), 3.33 nCi of [$^{14}$C]Oleoyl CoA, 403 µM of 1,2-dioleoyl-sn-glycerol, ethanol, acetone, and chloroform at the indicated concentration for each reaction. N-(7,10-dimethyl-1,1-oxo-10,11-dihydro-dibenzo[b,f][1,4]oxazepin-2-yl)-4-hydroxy-benzamide was made up in DMSO to 100x and diluted to final indicated concentrations. Values represent averages, n=3 ± SEM.

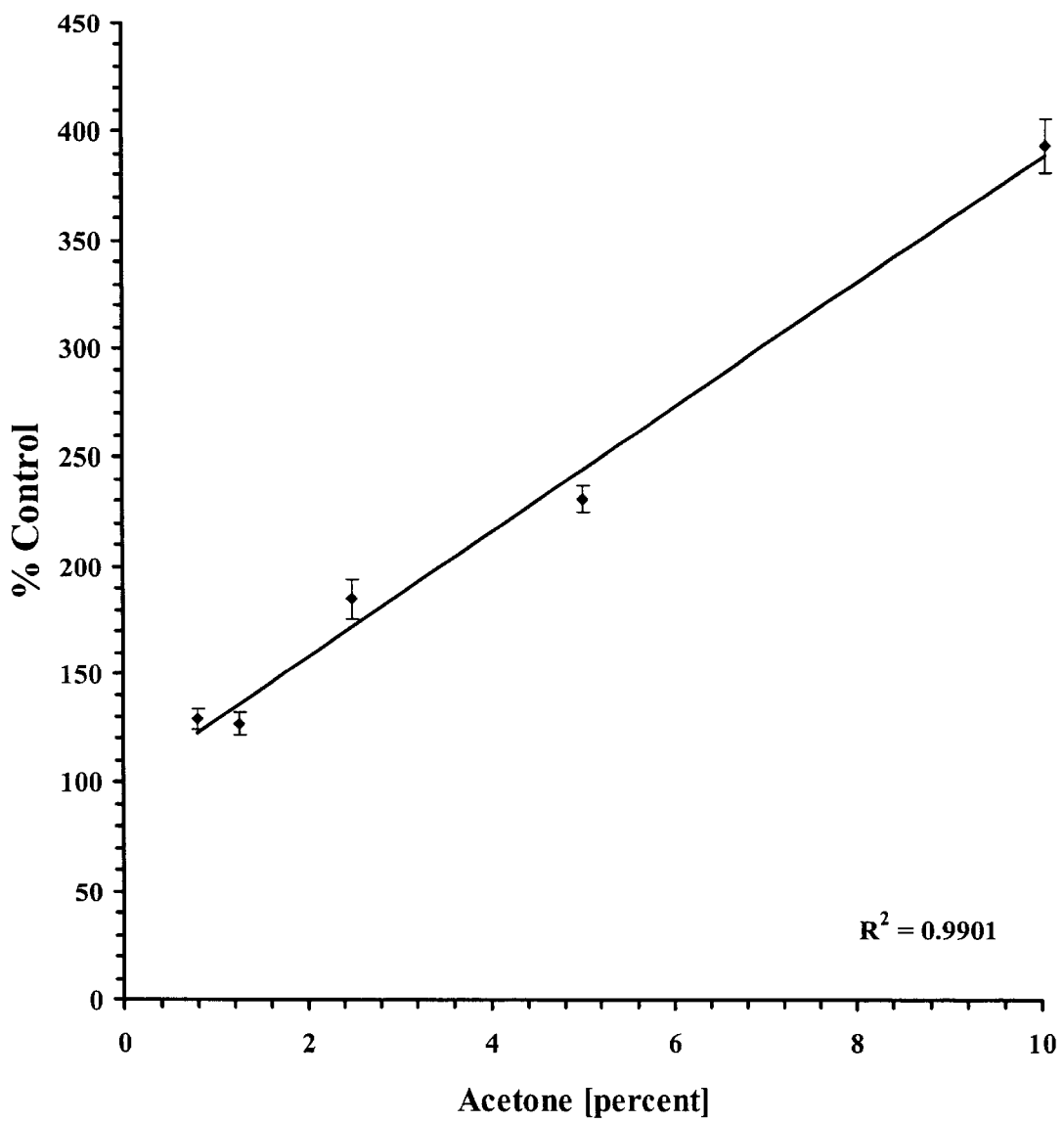
Figure 1B. Effect of Acetone on DGAT Activity

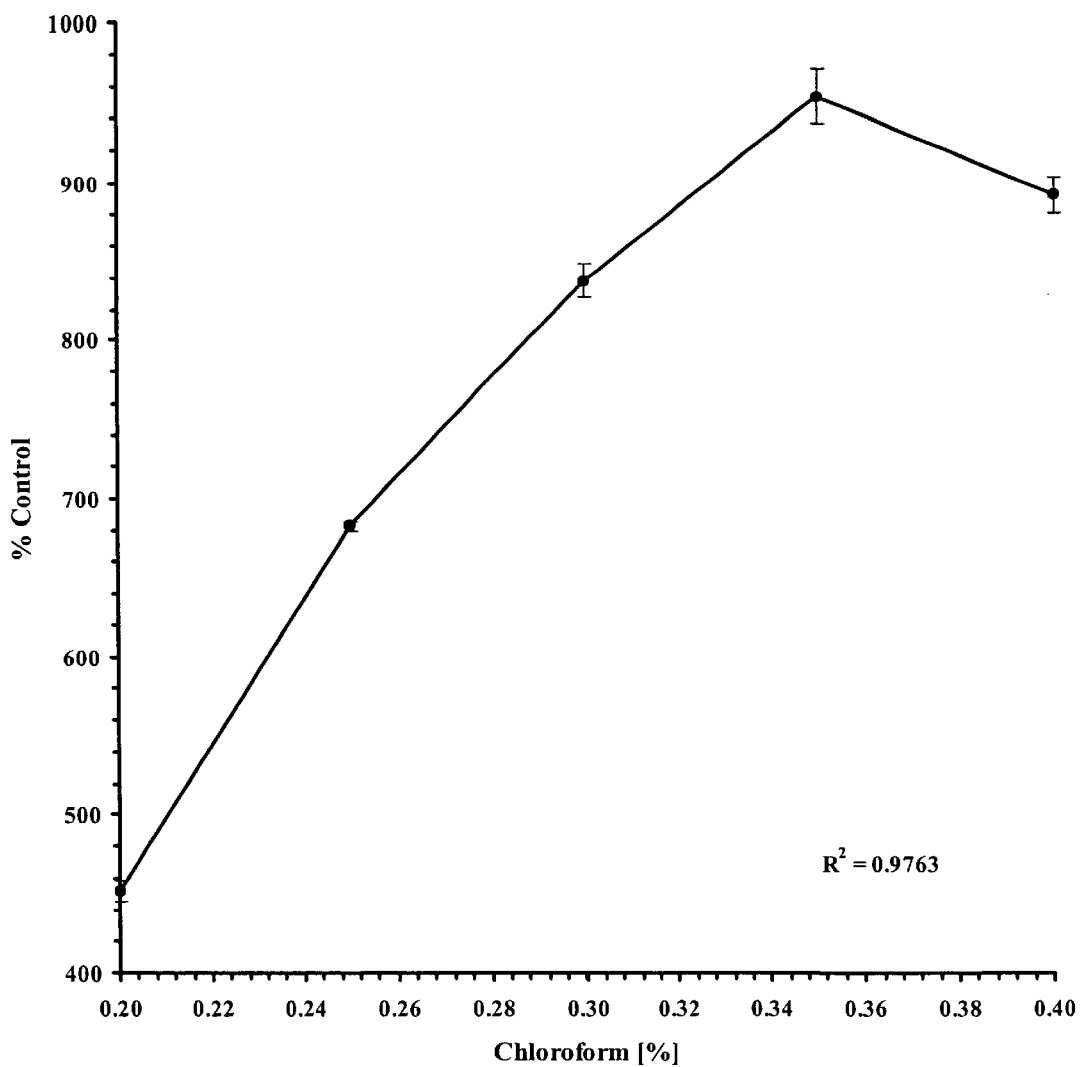
Figure 1C. Effect of Chloroform on DGAT Activity

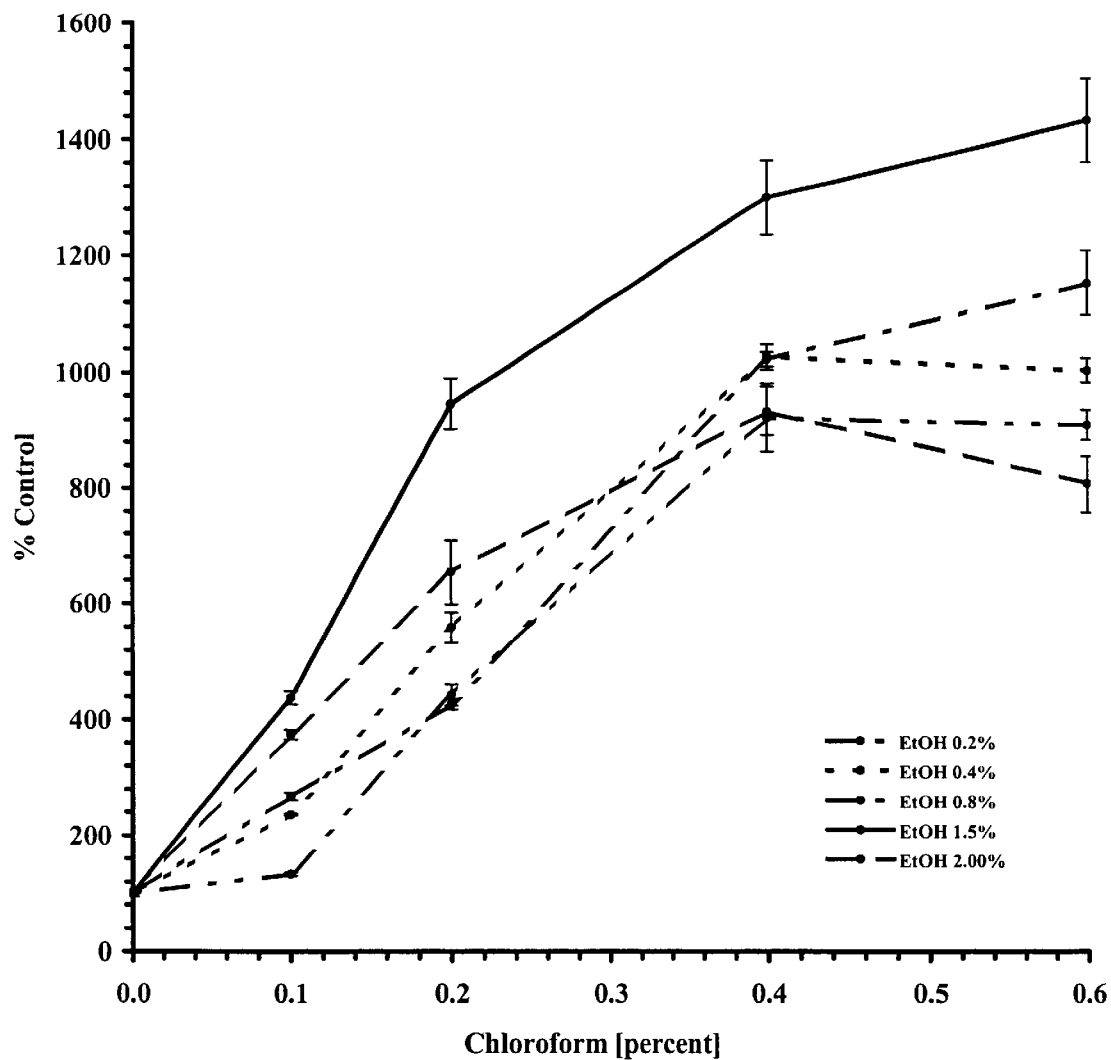
Figure 1D. Effect of Ethanol and Chloroform on DGAT Activity

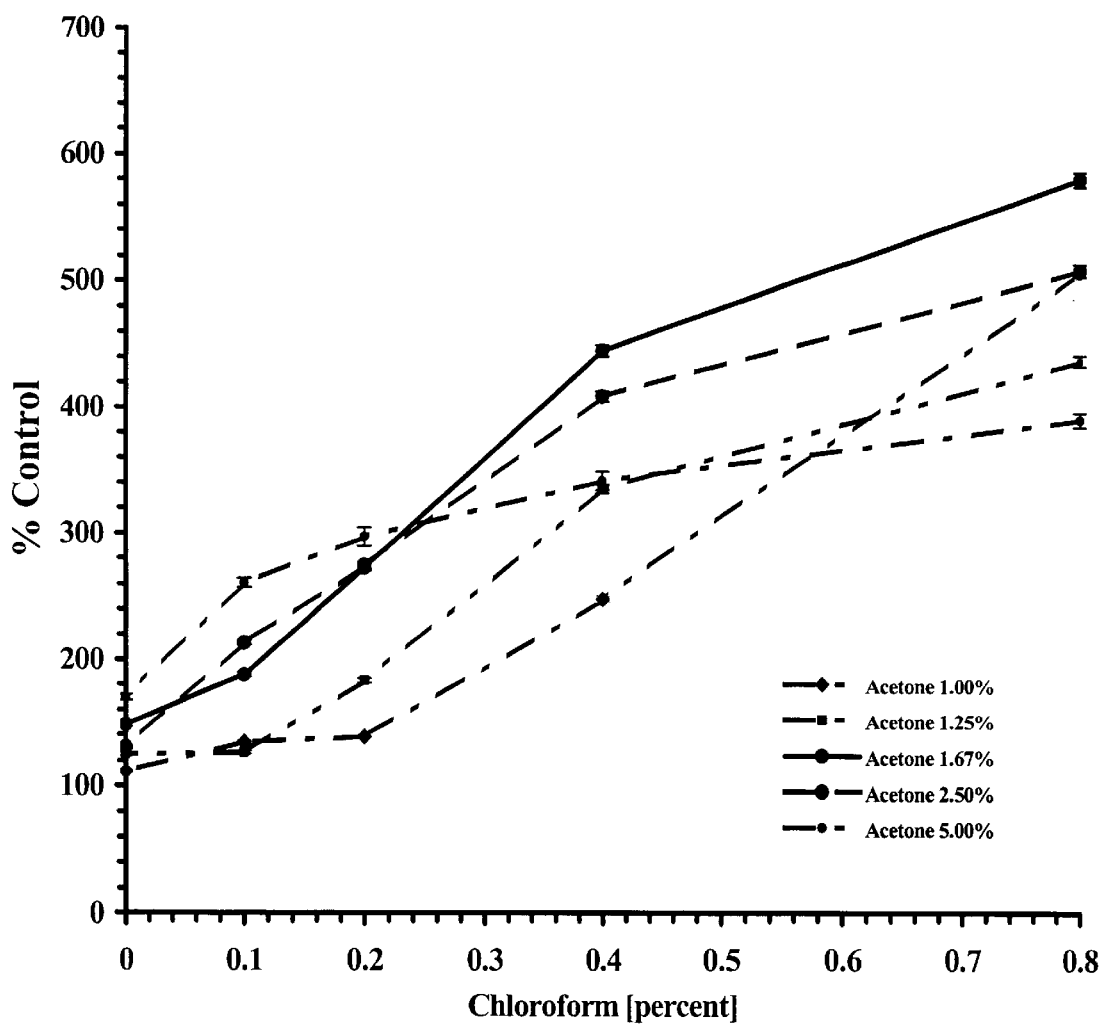
Figure 1E. Effect of Acetone and Chloroform on DGAT Activity

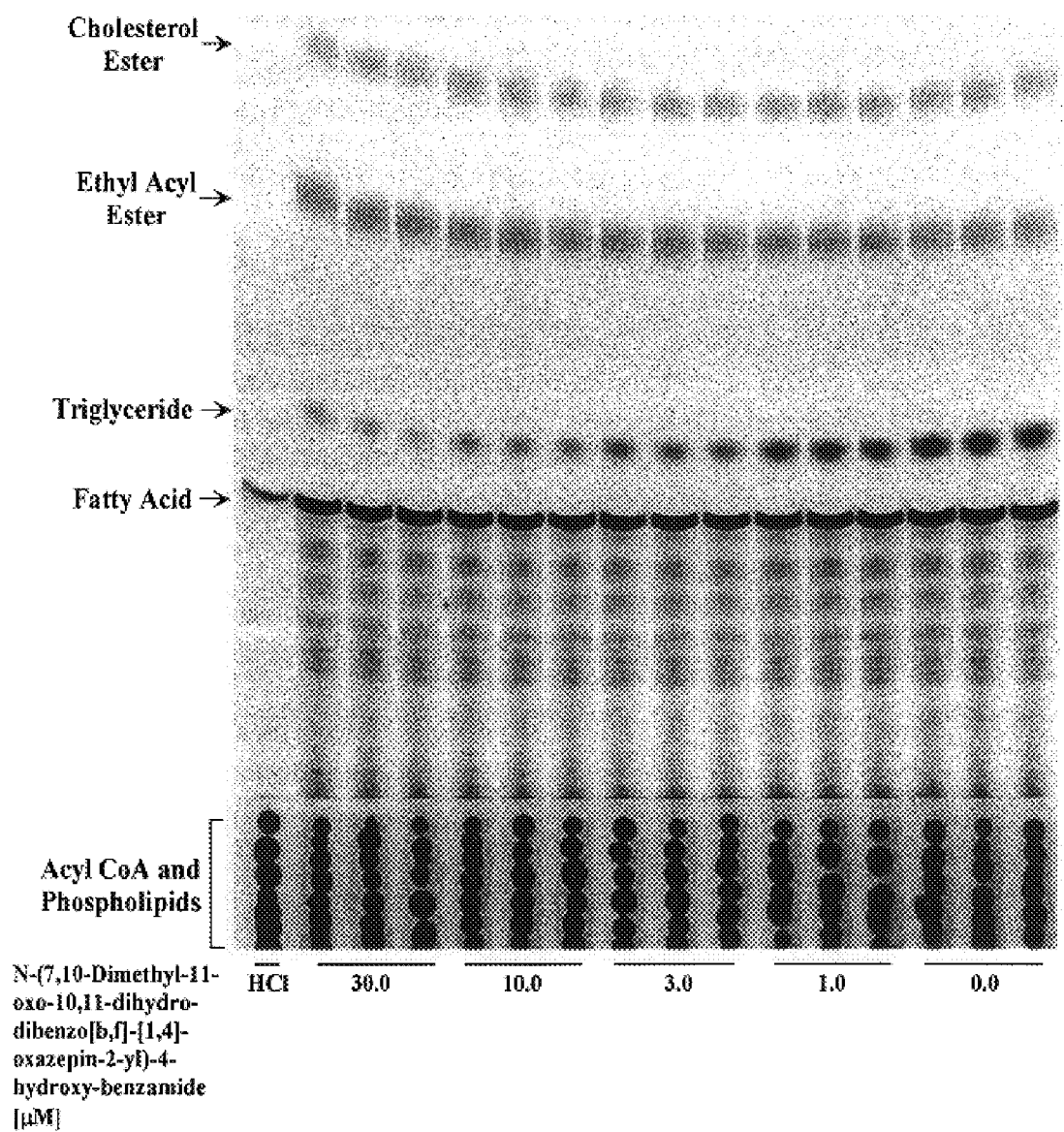
Figure 2A. DGAT Assay Comparing 0.8% Ethanol, TLC

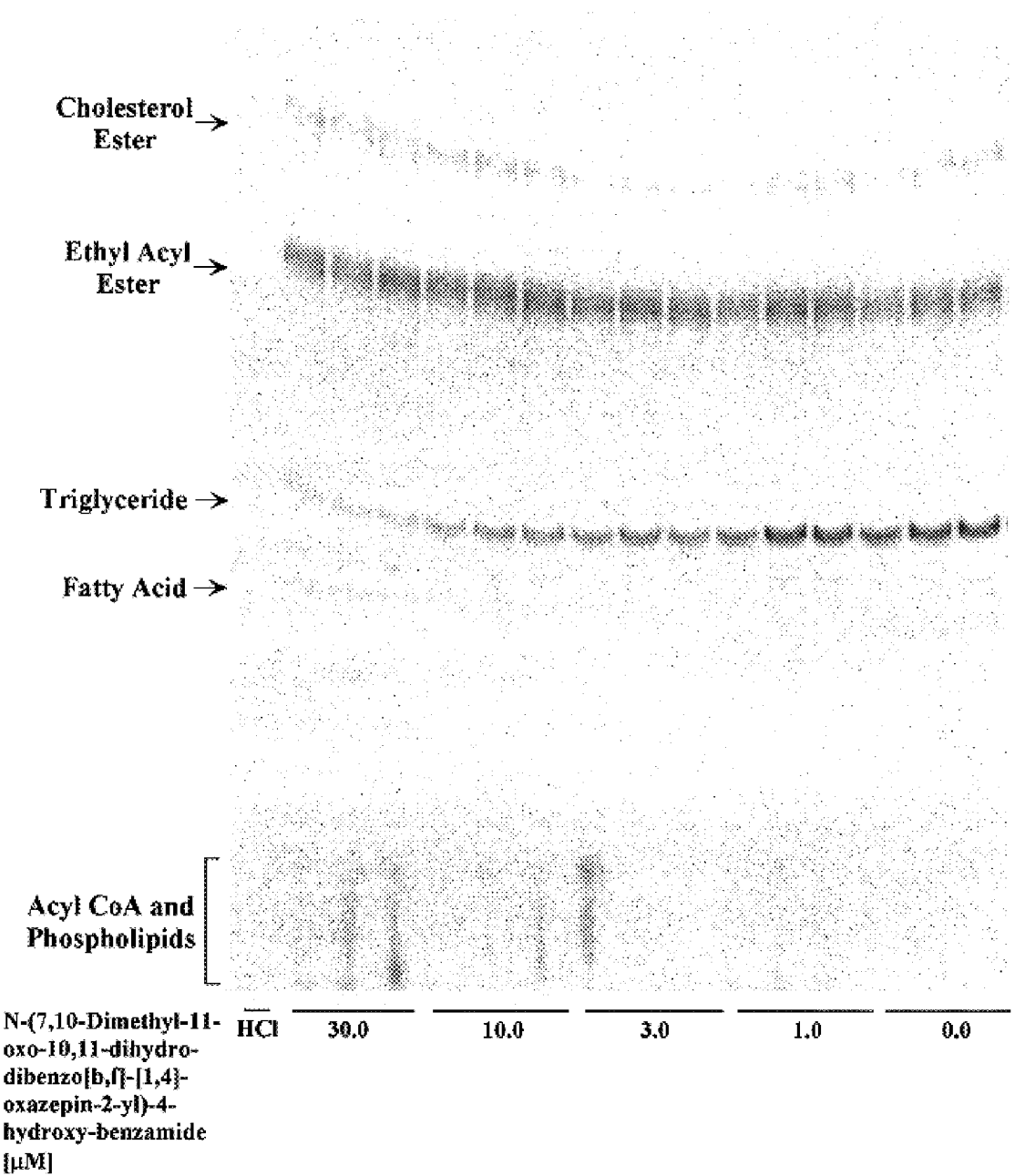
Figure 2B. DGAT Assay Comparing 0.8% Ethanol, 1-Step Extraction, TLC

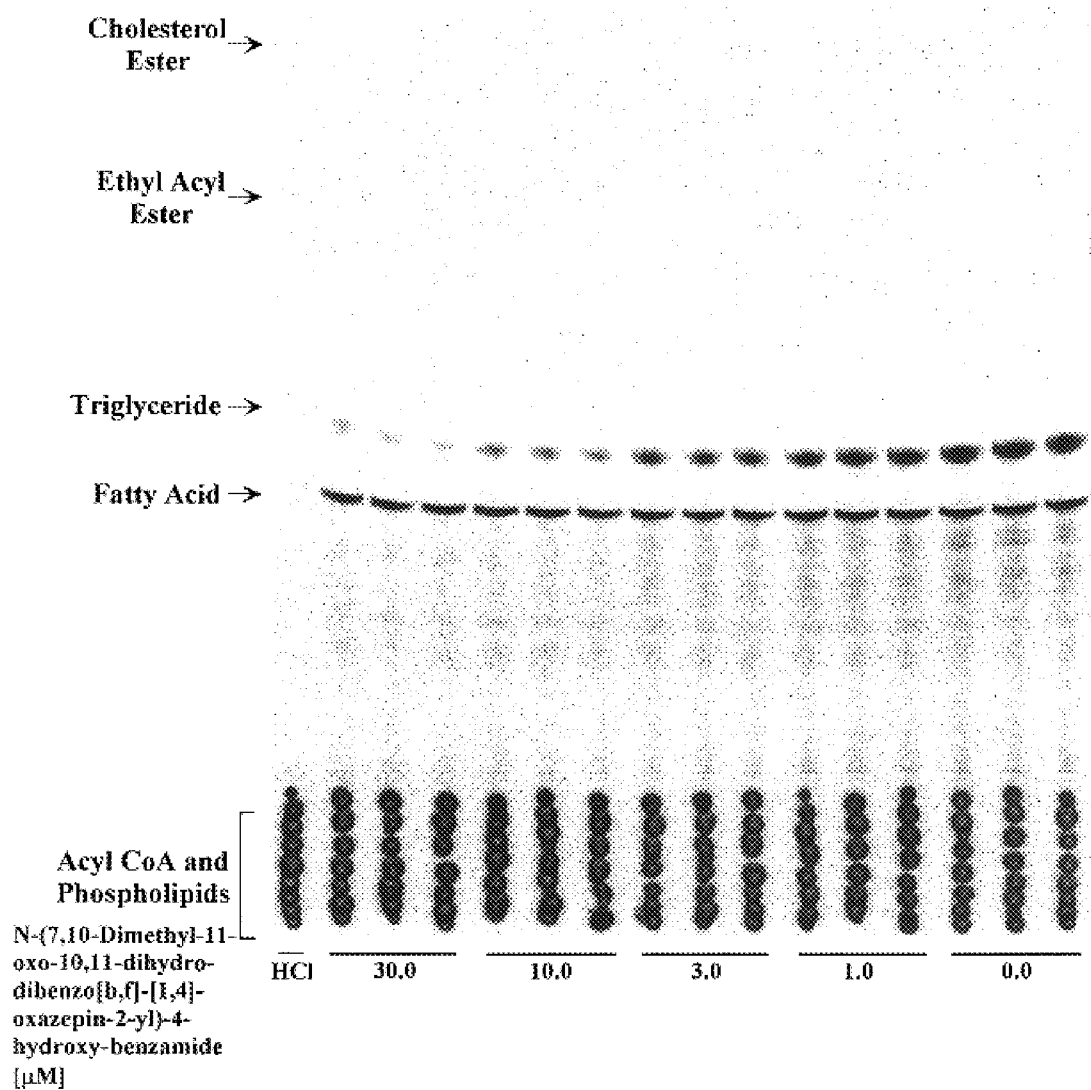
Figure 2C. DGAT Assay Comparing 2.1% Acetone:Chloroform (8:2), TLC

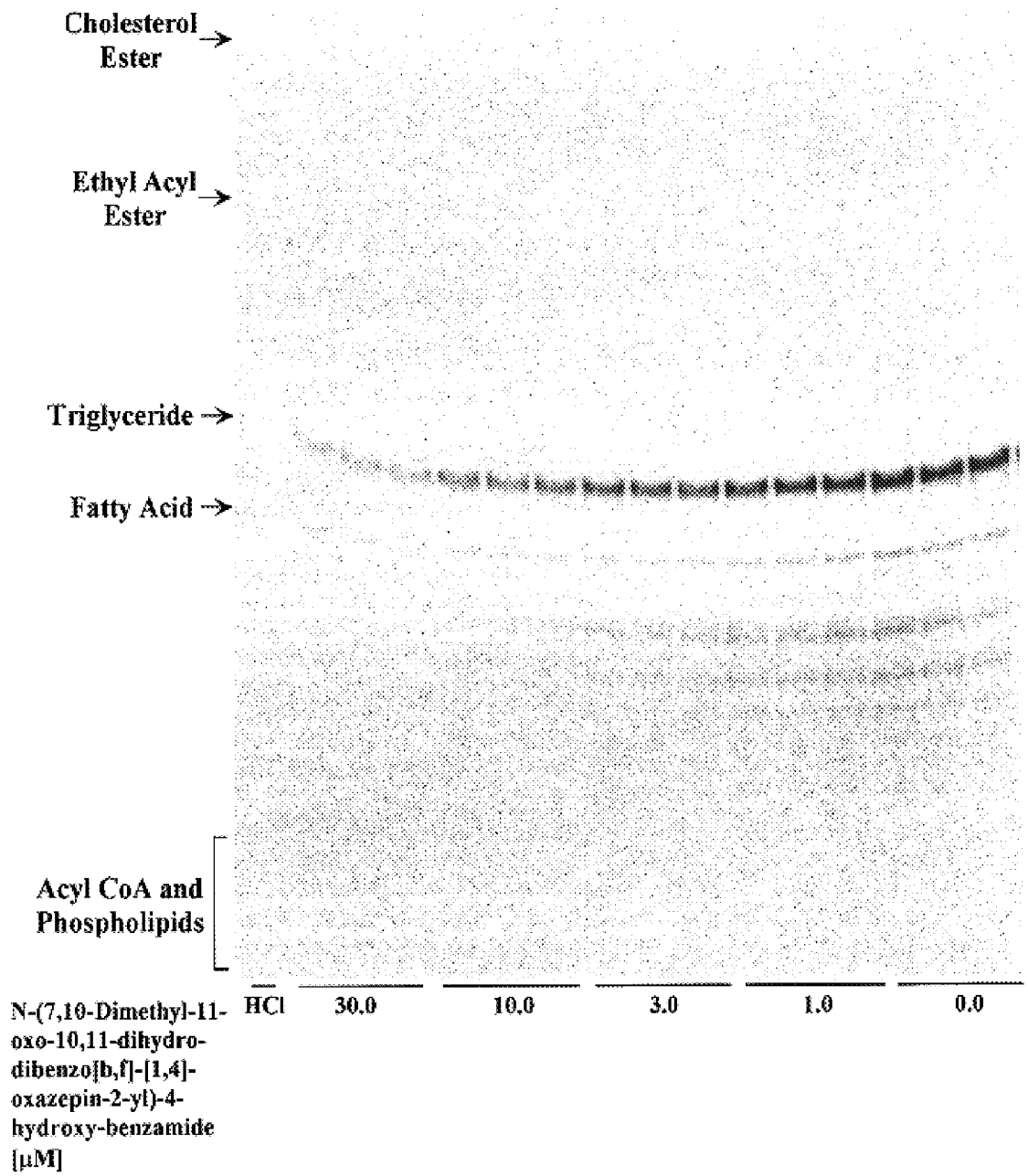
Figure 2D. DGAT Assay Comparing 2.1% Acetone:Chloroform (8:2), 1-Step Extraction, TLC

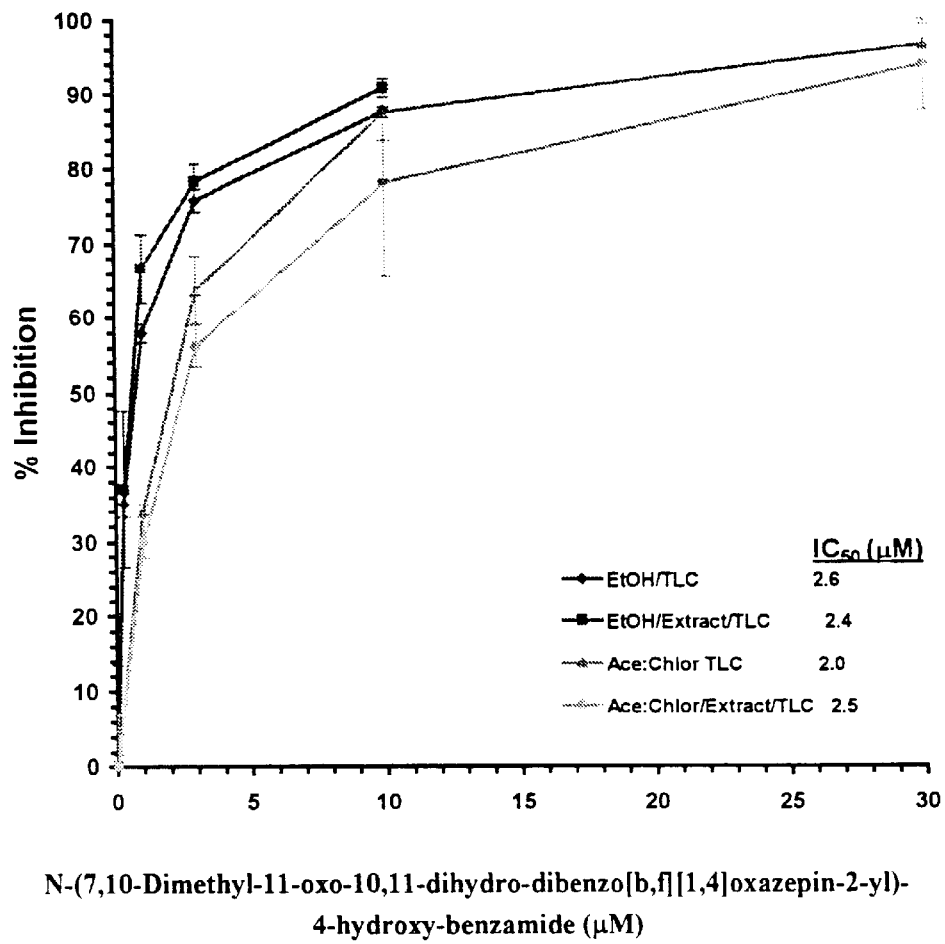

N-(7,10-Dimethyl-11-oxo-10,11-dihydro-dibenzo[b,f][1,4]oxazepin-2-yl)-
4-hydroxy-benzamide (µM)

Figure 3. DGAT Assay Using Direct Comparison Between 0.8% Ethanol and 2.1% Acetone:Chloroform (8:2), TLC Vs 1-Step Extraction Using N-(7,10-Dimethyl-11-oxo-10,11-dihydro-dibenzo[b,f][1,4]-oxazepin-2-yl)-4-hydroxy-benzamide Assays were performed at 37°C for 5 minutes using 40 µg microsomal protein, 20 nCi [$^{14}$C]oleoyl CoA, and 403 µM 1,2-dioleoyl-sn-glycerol per reaction for 0.8% ethanol and 1.25 µg microsomal protein, 8.3 nCi [$^{14}$C]oleoyl CoA and 403 µM 1,2-dioleoyl-sn-glycerol per reaction for 2.1% acetone:chloroform. Values represent averages, n = 3 ± SEM.

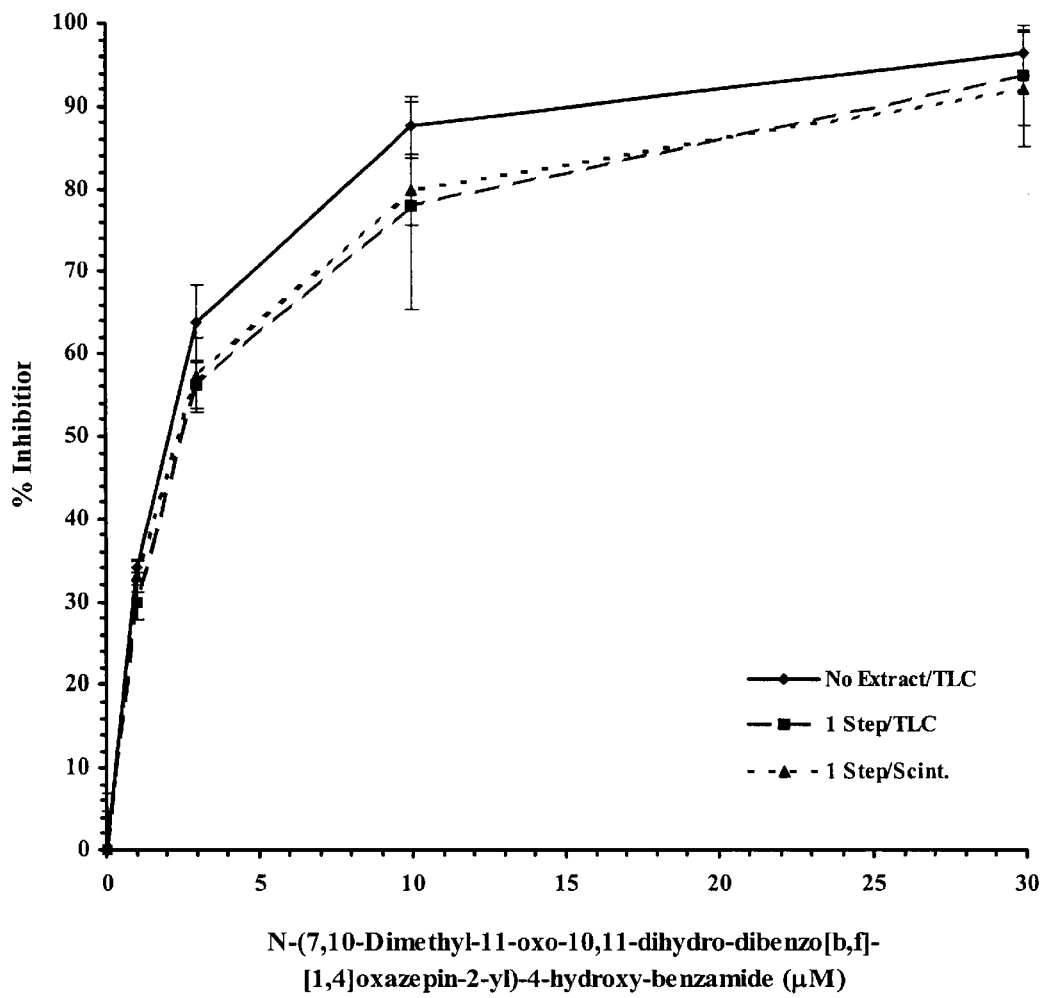

Figure 4A. Effect of N-(7,10-dimethyl-1,1-oxo-10,11-dihydro-dibenzo[b,f][1,4]oxazepin-2-yl)-4-hydroxy-benzamide on DGAT Activity from Group 1

Assays related to Figures 4 A-D were performed at 37 °C for 5 minutes using 1.25 μg of microsomal protein, 8.3 nCi of [$^{14}$C]Oleoyl CoA and 403 μM of 1,2-dioleoyl-sn-glycerol per reaction. [$^{14}$C]Tryglyceride was measured either by TLC alone, 1-Step Extraction and TLC, or 1-Step Extraction and scintillation counting. Values represent averages, n=3 ± SEM.

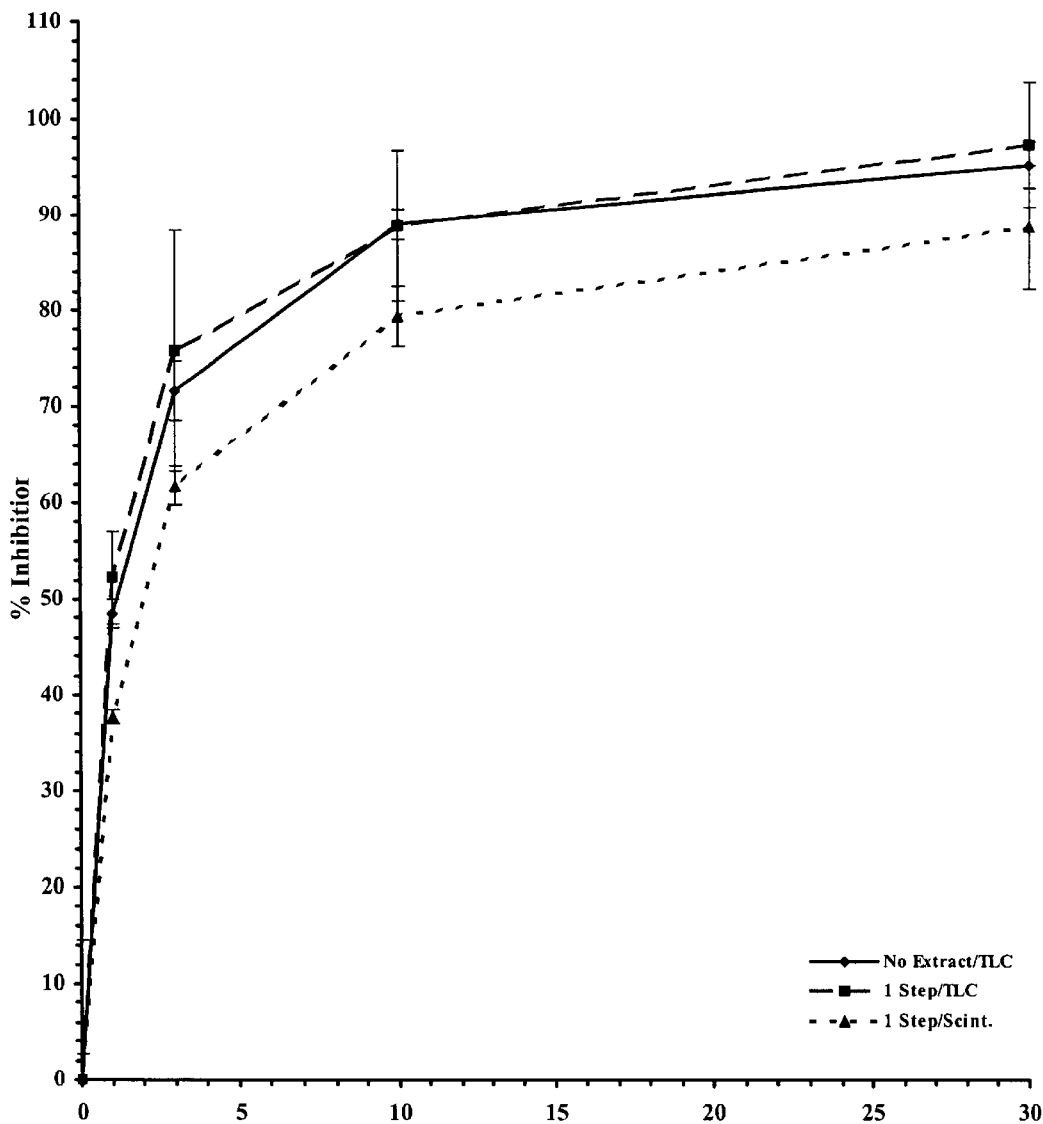
Figure 4B. Effect of N-(7,10-dimethyl-1,1-oxo-10,11-dihydro-dibenzo[b,f][1,4]oxazepin-2-yl)-4-hydroxy-benzamide on DGAT Activity from Group 2

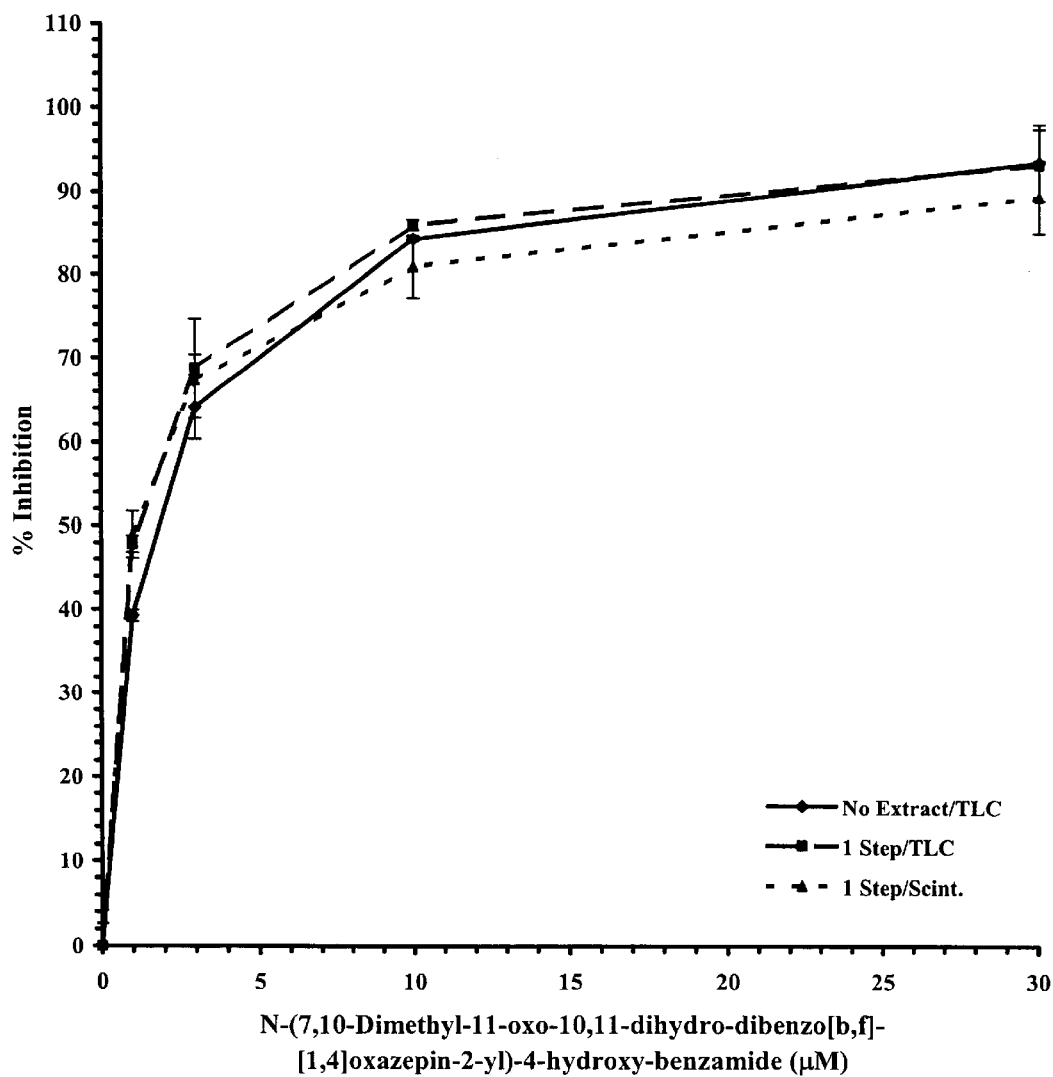
Figure 4C. Effect of N-(7,10-dimethyl-1,1-oxo-10,11-dihydro-dibenzo[b,f][1,4]oxazepin-2-yl)-4-hydroxy-benzamide on DGAT Activity from Group 3

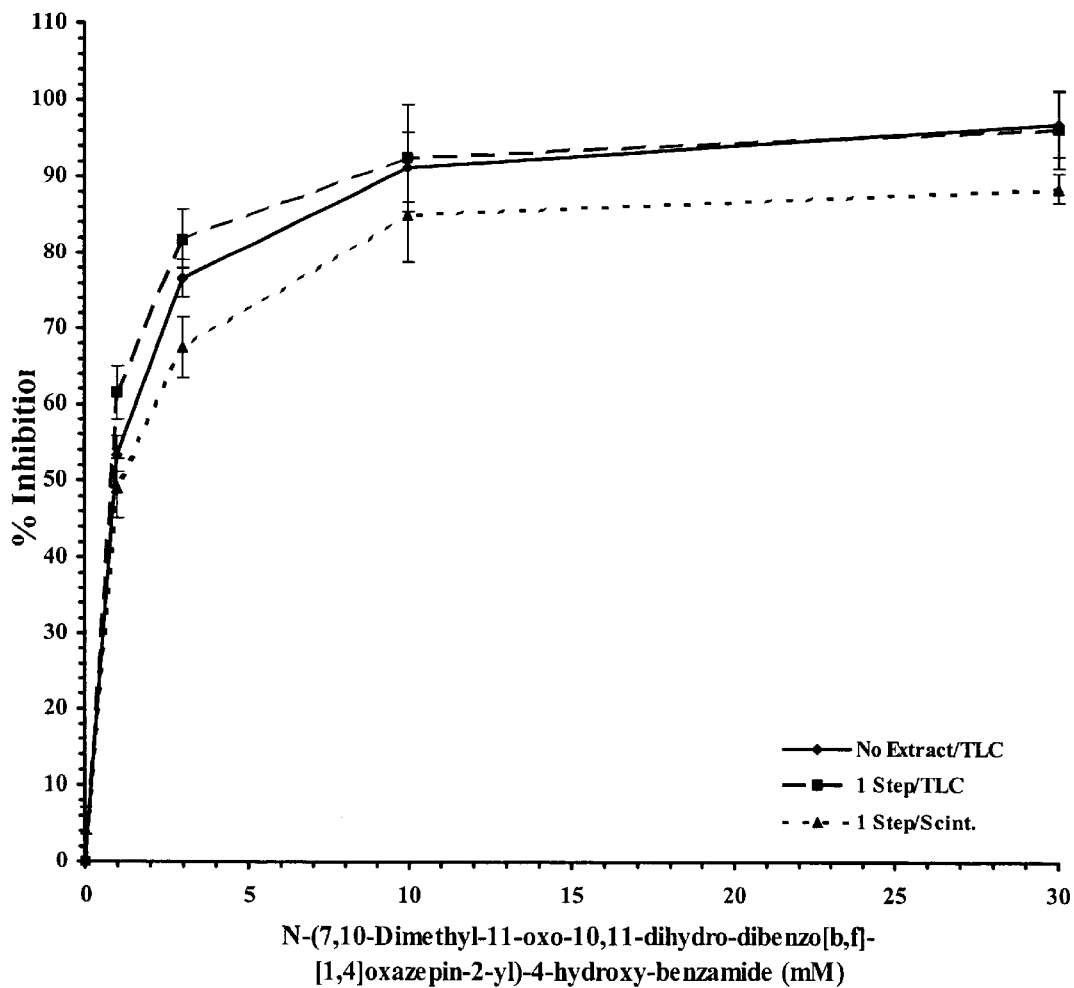
Figure 4D. Effect of N-(7,10-dimethyl-1,1-oxo-10,11-dihydro-dibenzo[b,f][1,4]oxazepin-2-yl)-4-hydroxy-benzamide on DGAT Activity from Group 4 Rat Liver Microsomes Preparations Comparing TLC, 1-Step Extraction/TLC , and 1-Step Extraction/Scintillatioin Counting

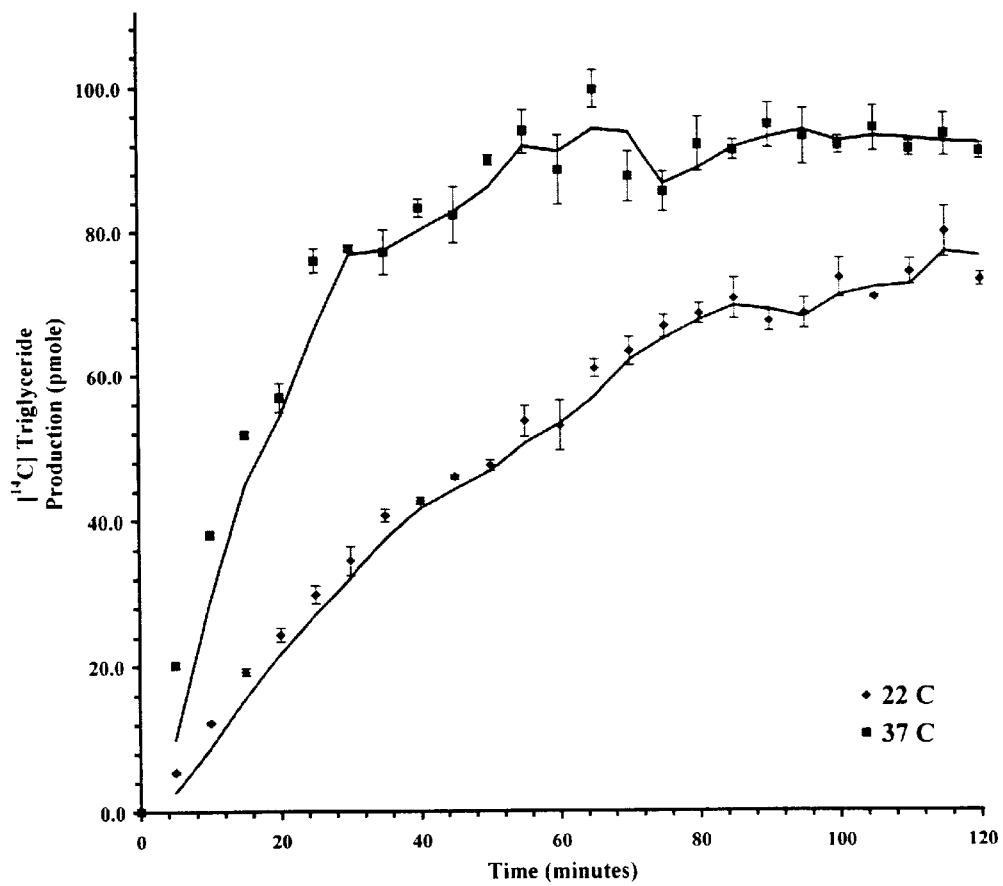
Figure 5. Effect of Time and Temperature on DGAT Activity
Assays were performed at 22°C or 37°C for the indicated times using 1.25 µg microsomal protein, 8.3 nCi [$^{14}$C]oleoyl CoA and 403 µM 1,2-dioleoyl-sn-glycerol per reaction. Values represent averages, n = 3 ± SEM.

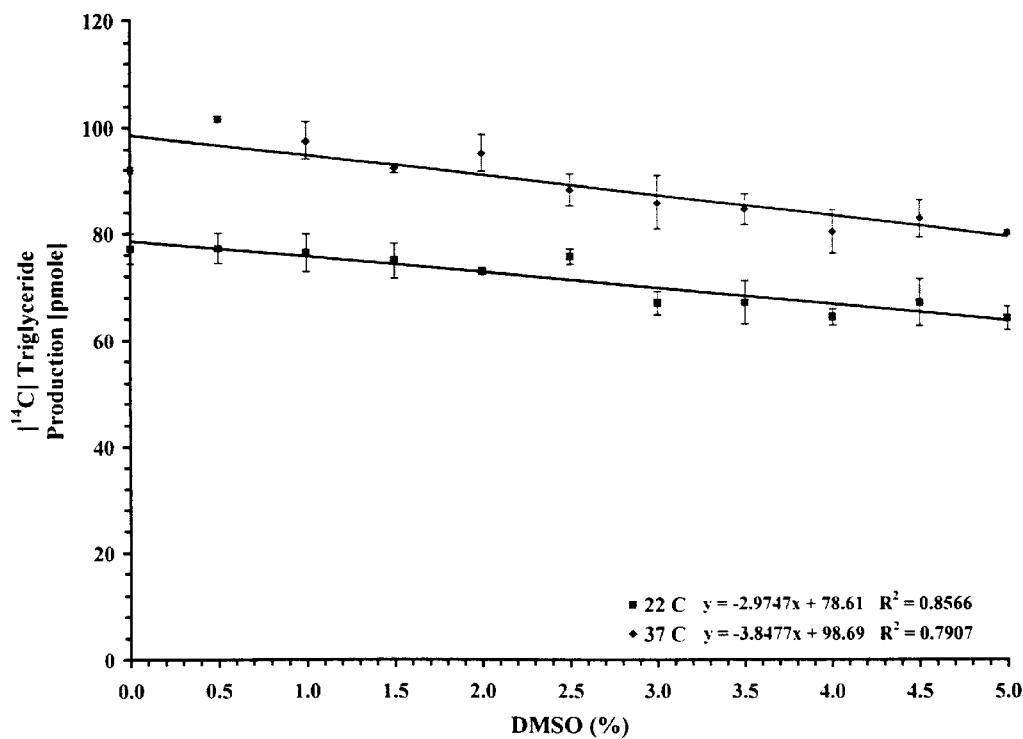
Figure 6. Effect of DMSO on DGAT Activity
Assays were performed at 22°C for 20 minutes or 37°C for 5 minutes using 1.25 µg microsomal protein, 8.3 nCi [14C]Oleoyl CoA, 403 µM 1,2-dioleoyl-sn-glycerol per reaction, and DMSO at the indicated concentrations. Values represent averages, n = 3 ± SEM.

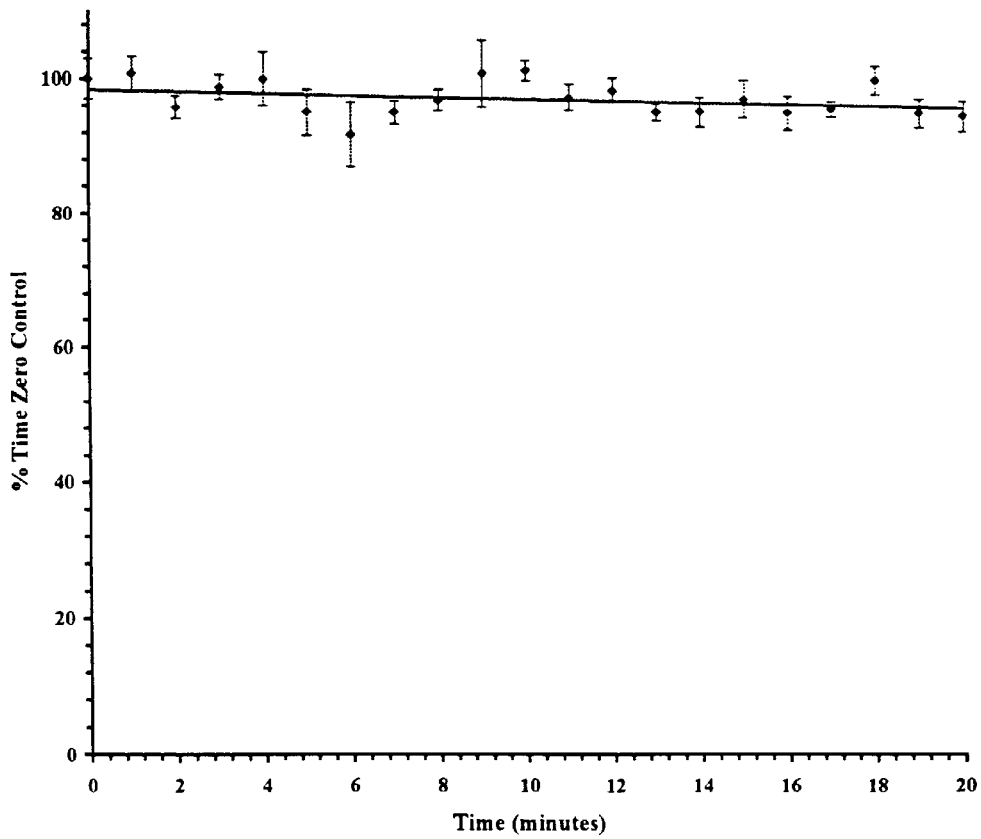

Figure 7. Effect of Alkaline Ethanol Stop Solution Mix (AESSM) on the Stability of [$^{14}$C]Triglyceride Produced in DGAT Assay Assays were performed at 37°C for 5 minutes using 1.25 µg microsomal protein, 8.3 nCi [$^{14}$C]oleoyl CoA and 403 µM 1,2-dioleoyl-sn-glycerol per reaction. Reactions were stopped by the addition of 150 µL of Alkaline Ethanol Stop Solution Mix (AESSM) and incubated at the indicated times at room temperature. Values represent averages, n = 3 ± SEM.

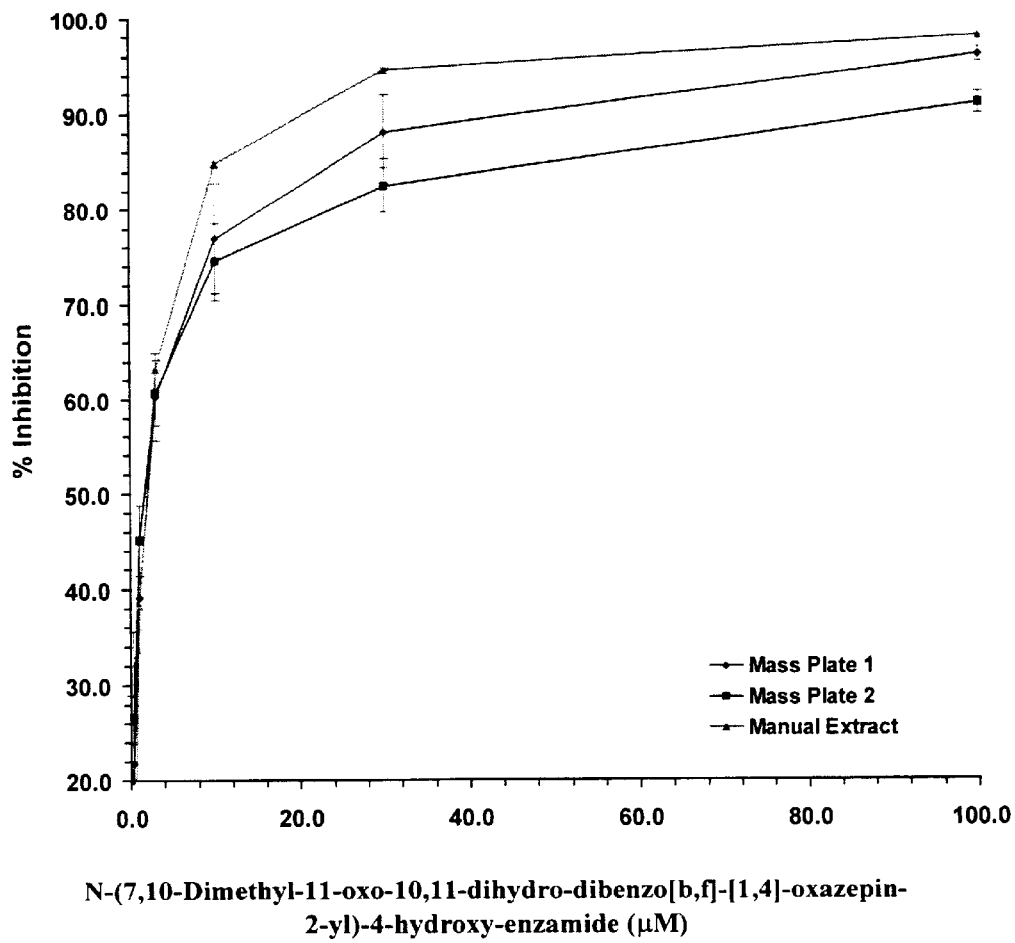

Figure 8. Effect of N-(7,10-Dimethyl-11-oxo-10,11-dihydro-dibenzo[b,f]-[1,4]oxazepin-2-yl)-4-hydroxy-benzamide on DGAT Activity As Measured By 96-Well Mass Screen Extraction and Manual Extraction Assays were performed at 22°C for 60 minutes using 1.25 μg microsomal protein, 8.3 nCi [$^{14}$C]oleoyl CoA and 403 μM 1,2-dioleoyl-sn-glycerol per reaction. Values for plate extraction represent averages, n = 6 ± SEM for plate 1 and n = 8 ± SEM for plate 2. Values for hand extraction represent averages, n = 2 ± SEM.

US 6,607,893 B2

DIACYLGLYCEROL ACYLTRANSFERASE (DGAT) ASSAY

This application claims the benefit of U.S. Provisional Application No. 60/258,681 filed Dec. 28, 2000.

FIELD OF THE INVENTION

The present invention generally provides a method of measuring the biological activity of diacylglycerol acyltransferase (DGAT). Specifically, the present invention provides a method for rapid, mass screening of compounds which are able to modulate the biological activity of DGAT. More specifically, the present invention provides an assay system for measuring DGAT activity which allows for greater DGAT activity while eliminating acyl CoA:acyltransferase (ACAT) and ethanol acyltransferase (EAT) activities as well as significantly reducing fatty acylhydrolase (AH) activity.

BACKGROUND OF THE INVENTION

Hypertriglyceridemia is a risk factor for the development of cardiovascular diseases (Gaziano J., Hennekens C., O'Donnell C, Breslow J., Buring J. Fasting triglycerides, high-density lipoprotein, and risk of myocardial infarction. Circulation 1997;96:2520–2525). Triglycerides (TG) also play an important role in the fat loading of adipocytes (Coleman R., Bell R. Triacylglycerol synthesis in isolated fat cells. *J. Biol. Chem.* 1976;251 :4537–4543), and therefore play a major role in obesity. Additionally, triglycerides are required for the assembly of apoB-100 containing lipoproteins such as VLDL and LDL (Bostrom K., Boren J., Wettesten M., et al. Studies on the assembly of apo B-100-containing lipoproteins in HepG2 cells. *J. Bio. Chem.* 1988;263:4434–4442; Pullinger C., North J., Teng B., Rifici V., Ronhild de Brito A; Scott J. The apolipoprotein B gene is constituitively expressed in HepG2 cells: regulation of secretion by oleic acid, albumin, and insulin, and measurement of the mRNA half-life. *J. Lipid Res.* 1989;30:1065–1077). Consequentially, there is considerable interest in developing therapies for lowering triglyceride levels. The enzyme known to catalyze the final/committed step in triglyceride biosynthesis is diacylglycerol acyltransferase (DGAT) (Coleman R. Diacylglycerol acyltransferase and monoacylglycerol acyltransferase from liver and intestine. *Methods in Enzymology* 1992;209:98–104). DGAT catalyzes the transfer of coenzymeA activated fatty acids to the 3 position of 1,2-diacylglycerols, forming a triglyceride molecule (Lehner R; Kuksis A. Biosynthesis of triacylglycerols. *Prog. Lipid Res.* 1996;35(No. 2):169–201; Bell R. Enzymes of glycerolipid synthesis in eukaryotes. *Ann Rev. Biochem.* 1980;49:459–487). Therefore, inhibition of DGAT activity would lead to decreased triglyceride production through this pathway, which would result in the concomitant lowering of plasma VLDL/LDL and possibly increases in HDL. However, a mass screen for the isolation of specific DGAT inhibitors has not been previously established due to technical difficulties associated with establishment of such an assay.

Conventional DGAT assays have low activities on the order of pmoles TG/min/mg microsomal protein and are contaminated by the products of several other enzymatic reactions. Furthermore, the product of the DGAT catalyzed reaction is usually resolved by TLC analysis, which is impractical for use in a mass screen. A method using organic solvents to extract DGAT generated TG from isolated microsomes has been previously described (Coleman R. A. Diacylglycerol acyltransferase and monoacylglycerol acyltransferase from liver and intestine. *Meth. Enzymology* 1992;209:98–104). However, several steps are involved in the extraction making this technique very difficult to adapt to a mass screen. Applicants have developed a solvent system comprising of acetone:chloroform or ethanol:chloroform which dramatically boosts DGAT activity while simultaneously suppressing the activity of interfering enzymes. In addition, a 1-step extraction method that specifically extracts TG from the DGAT catalyzed reaction mixture has been developed. To screen for modulators of DGAT activity, applicants have modified the DGAT assay of the present invention and have altered the 1-step extraction method of the present invention into a 96-well format that allows for high throughput screening modulators/compounds. These modifications enable the DGAT assay to be automated, i.e., to be carried out by a robot.

SUMMARY OF THE INVENTION

The present invention provides a method for measuring diacylglycerol acetyltransferase (DGAT) activity which utilizes a novel solvent system to reduce and/or eliminate the activities of related or interfering compounds.

The present invention also discloses a method for determining whether a compound is useful for modulating DGAT biological activity. The method is capable of being utilized for mass screening of compounds as modulators of the biological activity of DGAT.

BRIEF DESCRIPTION OF THE FIGURES

FIG. 1 shows graphs of the effects of various solvents on microsomal enzyme activities including DGAT, wherein (A) shows the effects of ethanol on microsomal activities; (B) shows the effects of acetone on DGAT activity; (C) shows the effects of chloroform on DGAT activity; (D) shows the effects of ethanol and chloroform on DGAT activity; and (E) shows the effects of acetone and chloroform on DGAT activity. All assays were performed at 37° C. for 5 minutes utilizing 40 µg of microsomal protein (ethanol, chloroform, ethanol:chloroform) or 1.25 µg of microsomal protein (acetone, acetone:chloroform), 33.3 nCi of [$^{14}$C]oleoyl CoA, 403 µM of 1,2-dioleoyl-sn-glycerol, and ethanol, acetone and chloroform at the indicated concentrations for each reaction. N-(7,10-Dimethyl-11-oxo-10,11-dihydro-dibenzo[b,f][1,4]-oxazepin-2-yl)-4-hydroxy-benzamide was made up in DMSO to 100 times and diluted to final indicated concentrations. Values represent averages, n=3±SEM.

FIG. 2 shows various DGAT assays comparing (A) 0.8% ethanol, TLC; (B) 0.8% ethanol, 1-step extraction, TLC; (C) 2.1% acetone:chloroform (8:2), TLC; (D) 2.1% acetone:chloroform (8:2), 1-step extraction, TLC.

FIG. 3 is a graph illustrating the percent inhibition of DGAT activity by the compound N-(7,10-dimethyl-11-oxo-10,11-dihydro-dibenzo[b,f][1,4]-oxazepin-2-yl)-4-hydroxy-benzamide utilizing various solvents including 0.8% ethanol and 2.1% acetone:chloroform (8:2) and also comparing TLC versus 1-step extraction. Assays were performed at 37° C. for 5 minutes using 40 µg microsomal protein, 20 nCi [$^{14}$C]oleoyl CoA, and 403 µM 1,2-dioleoyl-sn-glycerol per reaction for 0.8% ethanol and 1.25 µg microsomal protein, 8.3 nCi [$^{14}$C]oleoyl CoA, and 403 µM 1,2-dioleoyl-sn-glycerol per reaction for 2.1% acetone:chloroform. Values represent averages, n=3±SEM.

FIG. 4 shows the effects of N-(7,10-dimethyl-11-oxo-10, 11-dihydro-dibenzo[b,f][1,4]oxazepin-2-yl)-4-hydroxy-benzamide on DGAT activity from (A) Group 1, (B) Group 2, (C) Group 3, and (D) Group 4 rat liver microbe preparations comparing TLC, 1-step extraction/TLC, and 1-step extraction/scintillation counting. Assays were performed at 37° C. for 5 minutes using 1.25 μg microsomal protein, 8.3 nCi [$^{14}$C]oleoyl CoA, and 403 μM 1,2-dioleoyl-sn-glycerol per reaction. [$^{14}$C]Triglyceride was measured either by TLC alone, 1-step extraction and TLC, or 1-step extraction and scintillation counting. Values represent averages, n=3±SEM.

FIG. 5 shows the effect of time and temperature on DGAT activity. Assays were performed at 22° C. or 37° C. for the indicated times using 1.25 μg microsomal protein, 8.3 nCi [$^{14}$C]oleoyl CoA, and 403 μM 1,2-dioleoyl-sn-glycerol per reaction. Values represent averages, n=3±SEM.

FIG. 6 shows the effects of DMSO on DGAT activity. Assays were performed at 22° C. for 20 minutes or 37° C. for 5 minutes using 1.25 μg microsomal protein, 8.3 nCi [$^{14}$C]oleoyl CoA, 403 μM 1,2-dioleoyl-sn-glycerol per reaction, and DMSO at the indicated concentrations. Values represent averages, n=3±SEM.

FIG. 7 shows the effect of Alkaline Ethanol Stop Solution Mix (AESSM) on the stability of [$^{14}$C]triglyceride produced in DGAT assay. Assays were performed at 37° C. for 5 minutes using 1.25 μg microsomal protein, 8.3 nCi [$^{14}$C] oleoyl CoA, and 403 μM 1,2-dioleoyl-sn-glycerol per reaction. Reactions were stopped by the addition of 150 μL of AESSM and incubated at the indicated times at room temperature. Values represent averages, n=3±SEM.

FIG. 8 shows the effect of N-(7,10-dimethyl-11-oxo-10, 11-dihydro-dibenzo[b,f][1,4]oxazepin-2-yl)-4-hydroxy-benzamide on DGAT activity as measured by 96-well mass screen extraction and manual extraction. Assays were performed at 22° C. for 60 minutes using 1.25 μg microsomal protein, 8.3 nCi [$^{14}$C]oleoyl CoA, and 403 μM 1,2-dioleoyl-sn-glycerol per reaction. Values for plate extraction represent averages, n=6±SEM for plate 1 and n=8±SEM for plate 2. Values for hand extraction represent averages, n=2±SEM.

DETAILED DESCRIPTION OF THE INVENTION

The present invention provides a method for measuring diacylglycerol acetyltransferase (DGAT) biological activity in an assay which allows for increased DGAT activity while at the same time greatly reducing and/or eliminating the activity of other reaction products or interfering products.

By "DGAT activity" is meant the transfer of coenzyme A activated fatty acids to the 3-position of 1,2-diacylglycerols, forming a triglyceride molecule.

As used herein, the term "triglyceride" (triacylglycerol or neutral fat) refers to a fatty acid triester of glycerol. Triglycerides are typically non-polar and water-insoluble. Phosphoglycerides (or glycerophospholipids) are major lipid components of biological membranes. The fats and oils in animals comprise largely mixtures of triglycerides.

As used herein, the term "modulate" is meant to increase or decrease a function. Preferably, a compound that modulates DGAT activity (e.g., triglyceride levels) does so by at least 10%, more preferably by at least 25%, and most preferably by at least 50% and can be defined as a "modulator" of DGAT activity.

The method generally includes the steps of combining at least one DGAT substrate with liver microsomes having DGAT associated therewith. The DGAT substrates and the microsomes are incubated together for a predetermined period of time. The preferred substrates for the present invention are a 1,2-diacylglycerol and a coenzymeA activated fatty acid. The method of the present invention preferably utilizes 1,2-dioleoyl-sn-glycerol and oleoyl CoA as the DGAT substrates.

The termination of the reaction of DGAT with its substrates can be accomplished by the addition of a solution comprising approximately 12.5% absolute ethanol, approximately 10% deionized water, approximately 2.5% of 1N NaOH, and approximately 75% of a solution comprising approximately 78.4% isopropanol, approximately 19.6% n-heptane, and approximately 2.0% deionized water.

Following termination of the reaction, the top (n-heptane) phase is analyzed for the presence of triglycerides as an indicator of DGAT biological activity. The presence of triglycerides can be detected and measured by utilizing phosphorimager plates or by utilizing scintillation counting. Preferably, the top phase is transferred to a phosphoimager plate, preferably a FLASH PLATE (NEN Life Sciences, Inc., Boston, Mass.) which is a 96-well plate or solid support comprised of a white polystyrene microplate in which the interior of each well is coated with a thin layer of polystyrene-based scintillant.

This process can be performed by automated machines or robots in order to increase the rate at which samples can be analyzed. In the present invention, as pointed out above, novel solvent systems are used to dissolve DGAT substrates. These particular solvent systems impart novel and advantageous properties to the method of the present invention. These properties include, but are not limited to, improved DGAT activity, enhanced DGAT selectivity and the ability to utilize a 1-step extraction in the method of the present invention.

DGAT has significantly enhanced activity with ethanol as the solvent between 0.5% to 4.0%, with acetone between 2.5% to 10%, with chloroform between 0.2% to 0.4%, and the combinations of ethanol and chloroform, 0.2% to 2.0% and 0.1% to 0.6%, respectively, and in the combination of acetone and chloroform, 1.0% to 5.0% and 0.1% to 0.8%, respectively. When compared to 0.8% Tween 80 the initial solvent used for 1,2-dioleoyl-sn-glycerol in the DGAT assay, DGAT activity for 0.8% ethanol, 10% acetone, 0.4% chloroform, 2.1% acetone:chloroform (8:2), and 0.8% ethanol:chloroform (1:1) increased 5.3-, 484-, 463-, 1,057-, and 1,143-fold, respectively. The combination of acetone:chloroform had the further advantage of eliminating ACAT and EAT activities as well as significantly reducing FAH activity by 9.4-fold. Using the acetone:chloroform solvents, the 1-step extraction method utilized in the present invention is capable of only extracting out triglycerides from the DGAT assay.

The method of the present invention can also be modified for use in determining whether a compound is useful for modulating DGAT biological activity. In order to ascertain the capacity of a compound to modulate DGAT biological activity, a compound to be analyzed for its ability to modulate DGAT activity is combined with the DGAT substrates and the microsomes. The remaining steps of the method are identical to those described above for the DGAT assay. The ability of the compound to modulate DGAT biological activity can be determined by a change in DGAT biological activity, relative to a control not contacted with the compound, which indicates that the compound modulates DGAT biological activity. That is, the increase, decrease or lack of change in the production of triglycerides from the combination of DGAT with the DGAT substrates, provides a direct and quantifiable measurement of the effect that a test compound has on DGAT biological activity.

The following examples further illustrate the present invention. These examples are intended merely to be illustrative of the present invention and are not to be construed as limiting.

EXAMPLES

Materials and Methods

Reagents and Chemicals

[$^{14}$C]Oleoyl CoA and [$^{14}$C]glycerol trioleate were obtained from Amersham (Buckinghamshire, England).

Acetone, chloroform, methanol, isopropanol, ethanol, diethyl ether, N-heptane, isooctane, glacial acetic acid, HCl, sucrose, imidizole, fatty acid free BSA, 50% NaOH solution, DMSO, KCl, $CaCl_2$, $MgCl_2$, 1,2-dioleoyl-sn-glycerol were obtained from Sigma Chemical Co. (St. Louis, Mo.).

1.0 M Tris HCl, pH 7.4 was obtained from Digene (Beltsville, Md.).

0.5 M EDTA, pH 8.0 was obtained from Ambion (Austin, Tex.).

All buffers were filter-sterilized using a 0.22-$\mu$ filter before use.

N-(7,10-Dimethyl-11-oxo-10,11-dihydro-dibenzo[b,f][1,4]-oxazepin-2-yl)-4-hydroxy-benzamide (Chemistry, PGRD, Ann Arbor, Mich.).

Dc Protein Assay was obtained from BioRad (Hercules, Calif.).

20×20 cm Whatman LK6D Silica Gel 60 A TLC Plates, Costar 3794 96-well polypropylene plates, and Costar 3956 96-midwell polypropylene plates were obtained from VWR (Chicago, Ill.).

FLASHPLATES® were obtained from NEN Life Science Products, Inc, (Boston, Mass.).

Robotic reagent reservoirs were obtained from TomTec Instrumentation (Hamden, Conn.).

Animals

Male Sprague-Dawley rats (Rattus rattus), 350 to 400 g, were obtained from Charles River (Willmington, Md.). Rats were housed in an Association for Assessment and Accreditation of Laboratory Animal Care International accredited facility and fed a chow diet for 2 weeks prior to harvest.

Instrumentation

Homogenizers: Polytron PT 3100; Gerald K. Keller Co., GT-21 Mixer/Homogenizer

Centrifuge: Beckman/Coulter Avanti J-30I

Ultracentrifuge: Beckman L8-80 M

Microplate Spectrophotometer: Molecular Devices Spetra Max Plus

Incubation: Perkin Elmer 9600 Thermocycler

Gravity Convection Oven, 1310, VWR

PhosphorImager: Molecular Dynamics Storm 860 PhosphorImager

Multimek 96 Robotic Pipetor, Beckman/Coulter

Multidrop 384, Titertek, Beckman/Coulter

Saigen Carousels, Beckman/Coulter

Orca Robotic Arm, Beckman/Coulter

Saigen Plate Sealer Model 041-03-00043, Beckman/Coulter

Topcount NXT, Microplate Scintillation, and Luminescence Counter, Packard Instrument Company Beckman/Sagian Core Systems Software, Beckman/Coulter Microbe Isolation Sucrose Gradient Method Rats were euthanized using $CO_2$ affixation; their livers were immediately removed and placed in ice-cold microsome buffer (MC buffer) consisting of 125 mM sucrose, 3.0 mM imidazole, pH 7.4. Livers were cut into approximately 10 pieces, placed into 20 mL of ice cold MC buffer per liver and homogenized on ice in a glass Dounce power homogenizer using 10 up-and-down strokes. Homogenates were centrifuged at 1700 rpm in a Beckman JA-14 rotor for 10 minutes at 4° C. The supernatant was removed and placed on ice. The pellet was resuspended in 4.0 mL MC buffer per liver, rehomogenized as described above, and centrifuged at 1700 rpm in a Beckman JA-14 rotor for 10 minutes at 4° C. This supernatant was combined with the previous supernatant and centrifuged at 13,000 rpm in a Beckman JA-14 rotor for 20 minutes at 4° C. The supernatant was transferred to new tubes on ice, and the pellet was discarded. The supernate was centrifuged at 35,000 rpm in a Beckman Ti-70 rotor for 60 minutes at 4° C., and the resulting pellet, containing microsomal membranes, was resuspended in ice cold MC buffer using 17 strokes of a glass Dounce power homogenizer. Microsomal protein concentrations were determined by the Dc Protein Assay, and BSA was used to generate the standard curve. Microsomes were diluted to final protein concentration of 10 to 20 mg/mL. Microsomes were aliquoted into 1.0-mL tubes and stored in a liquid $N_2$ cryofreezer.

DGAT Enzyme Assay

Reagents

DGAT Assay Buffer (DAB): 0.25 M sucrose, 1.0 mM EDTA, pH 8.0, 150 mM Tris-HCl, pH 7.4, and 1.25 mg/mL fatty acid free BSA.

DGAT Assay Substrate Mixtures

[$^{14}$C]Oleoyl CoA and 1,2-dioleoyl-sn-glycerol dissolved in solvents (Tween 80, 100% nondenatured ethanol, acetone, chloroform, acetone:chloroform, ethanol:chloroform) are diluted into DAB at the indicated concentrations, the solution vortexed and kept on ice until the assay was performed.

Compounds were dissolved in DMSO and diluted to make 10x with DAB (10xcompound) and kept at room temperature until the assay was performed.

Frozen aliquots of microsomes (10–20 mg/mL total protein) were thawed on ice and diluted to make a 5x working stock at the indicated concentrations with MC buffer and stored on ice until use.

1-Step Extraction Solutions

Stop Solution: 78.4% isopropanol, 19.6% n-heptane, and 2.0% DI $H_2O$ was made in advance and stored in tightly sealed containers at room temperature for up to 1 month.

Alkaline Ethanol Stop Solution Mix (AESSM): 12.5% of 100% nondenatured ethanol, 10.0% DI $H_2O$, 2.5% 1.0N NaOH, 75.0% Stop Solution, made fresh prior to assay and stored at room temperature.

Reaction Procedure

The DGAT assay reaction was performed as follows: 5 $\mu$L of 10x compound was added to Perkin Elmer thin-walled reaction tubes followed by 35 $\mu$L of DGAT substrate mixture and vortexed. The reaction was started by the addition of 10 $\mu$L of the diluted 5x microsomes, vortexed, and incubated in a Perkin Elmer 9600 thermocycler for the indicated times and temperatures.

Triglyceride Separation

TLC Method

Reactions were stopped by the addition of 10 $\mu$L of 0.75N HCl. Samples were then spotted onto TLC plates and dried in a gravity convection oven at 70° C. for 30 minutes. Plates were developed in a 27×7.5×26 cm TLC chamber for 60 minutes at room temperature in 102 mL of isooctane:ethyl ether:acetic acid (75:25:2) for triglyceride determination. TLC plates were removed from the chamber, dried in a gravity convection oven at 70° C. for 30 minutes, wrapped in cellophane, and exposed to phosphorimager plates overnight. Phosphorimager plates were scanned on a phosphorimager and images were analyzed using ImageQuant software. A [$^{14}$C]glycerol trioleate standard was titrated onto TLC plates for mass determinations. All statistics were performed using Microsoft Excel's analysis software using a two-tailed t-test for means.

1-Step Extraction Method

Reactions were stopped by the addition of 150 μL of AESSM followed by the addition of 300 μL of n-heptane. The mixture is pipetted 5× to mix and allowed to separate for 5 minutes at room temperature. The entire top phase, n-heptane phase, is removed to new tubes and spotted onto silica TLC plates and processed as described above (see TLC method) or placed into 5-mL scintillation vials containing scintillation cocktail and counted.

96-Well DGAT Mass Screen Assay

Reagents

DGAT substrate mix consists of [$^{14}$C]oleoyl CoA 50 μCi/mL diluted to 278 nCi/mL and 1,2-dioleoyl-sn-glycerol dissolved in acetone:chloroform (8:2) 19.5 mM, diluted to 672 nM into DAB, vortexed, and stored on ice until the assay was performed.

Frozen aliquots of microsomes (10-20 mg/nl total protein) were thawed on ice and diluted to make 0.0625 mg/mL working stock with DAB and stored on ice until the assay was performed.

Reaction Protocol

Compounds were ordered from Compound Management, PGRD, Ann Arbor, dissolved in DMSO at 10 mM with 1.0 μL spotted into 96-well round bottom polypropylene plates. Plates are loaded onto the robot carousel. The robotic arm transfers the plates to a multidrop 1 for addition of 30 μL of substrate mix, and shaken for 1.0 minute at room temperature. The robot arm transfers the plate to multidrop 2 for the addition of 20 μL of diluted microsomes and shaken for 1.0 minute at room temperature. The robot arm transfers the plate back to the carousel where it incubates for 1.0 hour at room temperature.

Extraction Protocol

The robot arm transfers the plate to multidrop 3 for the addition of 150 μL of AESSM. The robot arm transfers the plate to the multimek to begin the extraction. The reaction volume is transferred to a 96-midwell polypropylene extraction plate on the multimek. The tips are washed 3×100 μL of DI H$_2$O in a reagent reservoir with a continuous flow of DI H$_2$O. The multimek then washes out the 96-well reaction plate with 3×100 μL of n-heptane and transfers the volume to the extraction plate. The multimek mixes the volume in the extraction plate 6×100 μL, and the plate sits for 10 seconds. The tips are washed 3×100 μL of DI H$_2$O in a continuous flow reagent reservoir. One hundred microliters of the top n-heptane phase is transferred to a Flash plate. The robot arm transfers the Flash plate to a carousel fitted with a fume hood, which allows the n-heptane to evaporate for a minimum of 6 hours. The plates are transferred to a plate sealer to be sealed, transferred to the top count scintillation counter, and counted for 1.0 minute. Data are collected and reported to the Trillium based compound management system.

Example 1

DAG Solvents

DGAT activity was measured using increasing amounts of these DAG solvents: ethanol, acetone, chloroform, and combinations of ethanol:chloroform or acetone:chloroform, where the acetone and ethanol concentrations were held constant while the chloroform concentrations were increased. DGAT activity increases with increasing concentrations of ethanol, $R^2=0.9626$, with a significant increase of 121% above control at 0.5% ethanol, p=0.013, to a level of 180% above controls at 4.0% ethanol, p=0.005 (FIG. 1A). DGAT activity also increases with increasing acetone concentrations, $R^2=0.9901$, to a level of 394% above controls at 10.0% acetone, p=0.0006 (FIG. 1B). DGAT activity increases with increasing concentrations of chloroform, $R^2=0.9763$, to a level of 955% of control at 0.35% chloroform, p=0.0004 (FIG. 1C). When using the combination of ethanol:chloroform, keeping ethanol at 1.5%, DGAT activity increases with increasing concentrations of chloroform, $R^2=0.9866$ and achieves a level of 1436% above control at 0.6% chloroform, p=0.0012 (FIG. 1D). When using the combination of acetone:chloroform, DGAT activity, with 1.67% acetone, is increased with increasing concentrations of chloroform, $R^2=1.000$ and achieves a level of 581% above control at 0.8% chloroform, p=0.003, although this increase ceases to be linear past 0.4% chloroform. The benefit of chloroform is diminished as the acetone concentration increases above 1.67% (FIG. 1E).

Known quantities of a [$^{14}$C]triacylglycerol (TAG), also known as triglyceride, standard were spotted onto TLC plates along with the DGAT reaction to determine the rate of [$^{14}$C]TAG production using the various DAG solvents. Production of [$^{14}$C]TAG ranged from 20±0.02 pmoles, 104±0.4 pmoles, 9.5±0.06 nmoles, 20.9±0.025 nmoles, and 22.5±0.58 nmoles [$^{14}$C]TAG/mg microbe protein/minute for 0.8% Tween 80, 0.8% ethanol, 10% acetone, 2.1% acetone:chloroform (8:2) and 0.8% ethanol:chloroform 1:1, respectively (Table 1). All values were significantly above or below the ethanol control, p<0.001.

Relative to Tween 80, all other solvents increased DGAT activity with the most dramatic being observed for the combination of acetone/chloroform or 95% ethanol/chloroform, 1057- and 1142-fold, respectively. However, acetone:chloroform (8:2) had the great advantage of eliminating ACAT and EAT activity and reducing FAH activity 9.4-fold (FIG. 3A) and (FIG. 3C). These benefits allowed the microbe concentration to be reduced 32-fold and the [$^{14}$C] oleoyl CoA substrate concentration could be decreased 12-fold from the initial conditions used to assay with DGAT.

Although the DGAT activity varied dramatically with the different solvents, the IC$_{50}$ of the reference compound, N-(7,10-dimethyl-11-oxo-10,11-dihydro-dibenzo[b,f][1,4] oxazepin-2-yl)-4-hydroxy-benzamide, was relatively constant ranging between 2.0 and 2.6 μM (Table 2).

Example 2

Comparison of the DAG Solvents Ethanol and Acetone:Chloroform (8:2) Using TLC and 1-Step Extraction Methods ACAT, EAT, FAH, and DGAT are active in the presence of 0.8% ethanol (FIG. 3A). When using the 1-step extraction protocol, the products of ACAT, cholesterol esters, and EAT, ethyl acyl esters, along with the triglycerides from DGAT are extracted (FIG. 3C). Using 2.1% acetone:chloroform (8:2) eliminates the products from ACAT and EAT and greatly reduces the activity of FAH, thereby increasing substrate availability for DGAT (FIG. 3C). Using 2.1% acetone:chloroform (8:2) in combination with the 1-step extraction method allows for the specific production and extraction of the [$^{14}$C]labeled triglycerides produced by DGAT (FIG. 3D). The IC$_{50}$ of the reference compound for DGAT inhibition, N-(7,10-dimethyl-11-oxo-10,11-dihydro-dibenzo[b,f][1,4]oxazepin-2-yl)-4-hydroxy-benzamide, ranges from 2.6 μM for the DGAT assay run with 0.8% ethanol and TLC, 2.4 μM for 0.8% ethanol extracted and run on TLC, 2.0 μM for 2.1% acetone:chloroform (8:2) and TLC to 2.5 μM for 2.1% acetone:chloroform (8:2) extracted and run on TLC (FIG. 3).

Example 3
Effect of N-(7,10-Dimethyl-11-oxo-10,11-dihydro-dibenzo[b,f][1,4] oxazepin-2-yl)-4-hydroxy-benzamide on DGAT Activity from Four Separate Rat Liver Microbe Preparations Comparing TLC, 1-Step Extraction/TLC and 1-Step Extraction/Scintillation Methods Four separate rat liver microbe preparations were used in a DGAT assay to compare the TLC and 1-step extraction methods, as well as comparing the phosphorimager and scintillation methods for detecting [$^{14}$C]triglyceride while using N-(7,10-dimethyl-11-oxo-10,11-dihydro-dibenzo[b,f][1,4]oxazepin-2-yl)-4-hydroxy-benzamide. The $IC_{50}$ for Groups 1, 2, 3, and 4 changed only marginally between the TLC method alone, the 1-step extraction/TLC, and the 1-step extraction/scintillation methods (FIG. 4 and Table 2).

Example 4
Time and Temperature on DGAT Assay

When running the DGAT assay at 22° C. for 2 hours, the production of [$^{14}$C]triglyceride increases in a linear manner up to 70 minutes, $R^2=0.9760$, and proceeds to level off past the 70 minutes to the final 120 minutes. When running the DGAT assay at 37° C. for 2 hours, the production of [$^{14}$C]triglyceride increases in a linear manner up to 25 minutes, $R^2=0.9758$, and proceeds to level off past the 25 minutes out to 120 minutes (FIG. 5).

Example 5
Effect of DMSO on DGAT Activity

DMSO decreases DGAT activity in a linear manner when DGAT is assayed at both 37° C., $R^2=0.8566$, and 22° C., $R^2=0.7907$. For both 37° C. a 22° C., the DGAT assay showed only significant changes when the DMSO concentration reached 4.5%, $p<0.05$ (FIG. 6).

Example 6
Effect of Alkaline Ethanol Stop Solution Mix (AAESS) on the Stability of [$^{14}$C]Triglyceride Produced in DGAT Assay During the running of the 96-well DGAT Mass Screen method, the DGAT reaction is terminated by the addition of AAESS, which contains 1.0N NaOH, and then incubates for a period of time, less than 5 minutes, while the robot transports the plate for extraction. Triglycerides are susceptible to hydrolysis in a basic environment, as would be found in the AAESS. When the DGAT reaction products are incubated at 22° C. in the presence of the AAESS, prior to extraction, the [$^{14}$C]triglyceride produced in the assay showed no significant decrease for incubations up to 20 minutes, $R^2=0.1225$, $p>0.05$ (FIG. 7).

Example 7
Effect of N-(7,10-Dimethyl-11-oxo-10,11-dihydro-dibenzo[b,f][1,4]oxazepin-2-yl)-4-hydroxy-benzamide on DGAT Activity Using the 96-well DGAT Mass Screen Method Compared to Manual Extraction The extraction protocol from the mass screen was run on two separate 96-well plates, 6 columns from the first plate, 8 columns from the second plate, and 2 columns from the first plate manually extracted, using the DGAT inhibitor N-(7,10-dimethyl-11-oxo-10,11-dihydro-dibenzo[b,f][1,4]oxazepin-2-yl)-4-hydroxy-benzamide. The $IC_{50}$ for plate 1, plate 2, and the manually extracted samples are 1.50, 1.27, and 1.70 μM, respectively (FIG. 8).

Applicants have tested a variety of parameters of the DGAT assay to develop a method that would allow for the mass screening of DGAT inhibitors without using TLC, a slow and laborious method. By using an acetone:chloroform solvent to dissolve the substrate, 1,2-dioleoyl-sn-glycerol, DGAT activity was increased over 1000-fold, ACAT and EAT activities were eliminated, and FAH activity was reduced over 9-fold. Using acetone:chloroform allowed for very high [$^{14}$C]triglyceride production, which facilitated its extraction by the 1-step extraction method. By adjusting the DGAT assay reagent volumes and the 1-step extraction method, the assay became amiable to a 96-well format. The latter modification allows for a high throughput screening mass screening of DGAT inhibitors. Time, temperature and DMSO concentrations best suited for the 96-well DGAT Mass Screen method were established. The DGAT inhibitor, N-(7,10-dimethyl-11-oxo-10,11-dihydro-dibenzo[b,f][1,4] oxazepin-2-yl)-4-hydroxy-benzamide, demonstrated the validity of the 96-well format assay to screen for DGAT inhibitors.

TABLE 1

Effect of Solvents on DGAT Activity.

| Solvent | % in Reaction | Activity (pmole TAG formed/ mg protein/min) | Fold Increase |
|---|---|---|---|
| Tween 80 | 0.8 | 20 ± 0.2 | 1.0 |
| 95% EtOH | 0.8 | 104 ± 0.4 | 5.3[a] |
| Acetone | 10 | 9,537 ± 62 | 483.5[a] |
| Chloroform | 0.4 | 9,256 ± 21 | 462.8 |
| Acetone:Chloroform (8:2) | 2.1 | 20,851 ± 248 | 1,057.0[a] |
| 95% EtOH:Chloroform (1:1) | 0.8 | 22,539 ± 581 | 1,142.5[a] |

Assays were performed at 37° C. for 5 minutes using 40 μg microsomal protein, 20 nCi[$^{14}$C]oleoyl CoA, and 403 μM 1,2-dioleoyl-sn-glycerol for ethanol and 1.25 μg microsomal protein, 8.3 nCi[$^{14}$C]oleoyl CoA, and 403 μM 1,2-dioleoyl-sn-glycerol for acetone:chloroform. Values represent averages, n = 3 ± SEM.
[a]p < 0.0001 vs Tween 80

TABLE 2

Effect of N-(7,10-Dimethyl-11-oxo-10,11-dihydro-dibenzo[b,f]-[1,4]oxazepin-2-yl)-4-hydroxy-benzamide on DGAT Activity From Four Separate Rat Liver Microsome Preparations Comparing TLC method, 1-Step Extraction/TLC, and 1-Step Extraction/Scintillation

| | Group 1 $IC_{50}$ [μM] | Group 2 $IC_{50}$ [μM] | Group 3 $IC_{50}$ [μM] | Group 4 $IC_{50}$ [μM] |
|---|---|---|---|---|
| TLC | 1.07 | 1.52 | 1.74 | 0.91 |
| 1-Step/TLC | 0.95 | 1.14 | 2.30 | 0.73 |
| 1-Step/Scintillation | 1.66 | 1.12 | 2.05 | 1.10 |

Assays were performed at 37° C. for 5 minutes using 1.25 μg microsomal protein, 8.3 nCi[$^{14}$C]oleoyl CoA, and 403 μM 1,2-dioleoyl-sn-glycerol per reaction.

The examples clearly demonstrate the utility of the method of the present invention for measuring DGAT activity and for the high throughput screening of compounds as modulators of DGAT activity.

In view of the foregoing, it will be understood and appreciated that numerous modifications and variations of the aforedescribed invention may be readily implemented. The discussion, description, and examples set forth herein are illustrative of particular embodiments of the present invention, but are not meant to be limitations upon the practice thereof. It is the following claims, including all equivalents, which define the scope of the invention.

What is claimed is:

1. A method for measuring diacylglycerol acetyltransferase (DGAT) activity, said method comprising the steps of:
   (a) providing at least one DGAT substrate;
   (b) combining microsomes having DGAT associated therewith with the DGAT substrate to form a reaction mixture;

(c) incubating the mixture of the microsomes and the DGAT substrate for a predetermined time interval;

(d) terminating the reaction of DGAT with the DGAT substrate; and (e) detecting triglyceride production as an indicator of DGAT biological activity.

2. The method according to claim 1, wherein the DGAT substrate comprises oleoyl CoA, 1,2-dioleoyl-sn-glycerol, and radioisotopes thereof.

3. The method according to claim 1, wherein the at least one DGAT substrate is dissolved in acetone:chloroform solvent.

4. The method according to claim 3, wherein the ratio of acetone to chloroform is 8:2.

5. The method according to claim 3, wherein the concentration of acetone ranges from approximately 1.0% to approximately 5.0%, by volume.

6. The method according to claim 3, wherein the concentration of chloroform ranges from approximately 0.1% to approximately 0.8%, by volume.

7. The method according to claim 1, wherein the DGAT substrates are dissolved in ethanol:chloroform solvent.

8. The method according to claim 7, wherein the ratio of ethanol to chloroform is 1:1.

9. The method according to claim 7, wherein the concentration of ethanol ranges from approximately 0.2% to approximately 2.0%, by volume.

10. The method according to claim 7, wherein the concentration of chloroform ranges from approximately 0.1% to approximately 0.6%, by volume.

11. The method according to claim 1, wherein the DGAT substrates are dissolved in ethanol.

12. The method according to claim 11, wherein the concentration of ethanol ranges from approximately 0.5% to approximately 4.0%, by volume.

13. The method according to claim 1, wherein the DGAT substrates are dissolved in acetone.

14. The method according to claim 13, wherein the concentration of acetone ranges from approximately 2.5% to approximately 10.0%, by volume.

15. The method according to claim 1, wherein the DGAT substrates are dissolved in chloroform.

16. The method according to claim 15, wherein the concentration of chloroform ranges from approximately 0.2% to approximately 0.4%, by volume.

17. The method according to claim 1, wherein said terminating step comprises adding a reaction termination agent to the mixture.

18. The method according to claim 17, wherein the termination agent comprises a mixture of ethanol, water, NaOH, and a solution comprising isopropanol, n-heptane, and water.

19. A method according to claim 18, wherein the solution comprises approximately 12.5% of absolute ethanol, approximately 10% deionized water, approximately 2.5% of 1N NaOH, and 75% of a stop solution comprising approximately 78.4% isopropanol, approximately 19.6% n-heptane, and approximately 2.0% deionized water.

20. A method according to claim 1, further including the step of (h) extracting the terminated reaction mixture with n-heptane.

21. A method according to claim 20, wherein said detecting step comprises performing thin layer chromatography on a sample of the extracted reaction mixture.

22. A method according to claim 20, wherein said detecting step further comprises the step of scintigraphically analyzing a sample of the reaction mixture.

23. A method according to claim 1, wherein the biological activity is triglyceride formation.

24. A method for determining whether a compound is useful for modulating diacylglycerol acyltransferase (DGAT) biological activity, said method comprising the steps of:

(a) providing DGAT substrates;

(b) providing microsomes having DGAT associated therewith;

(c) contacting a compound to be analyzed for its ability to modulate DGAT biological activity with the substituents set forth in (a) and (b) to form a reaction mixture;

(d) incubating the reaction mixture for a predetermined time interval;

(e) terminating any reaction of DGAT with the at least one DGAT substrate in the reaction mixture; and (f) measuring DGAT biological activity, wherein a change in DGAT biological activity, relative to a control not contacted with the compound, indicates that the compound modulates DGAT biological activity.

25. The method according to claim 24, wherein the DGAT substrate comprises oleoyl CoA, 1,2-dioleoyl-sn-glycerol, and radioisotopes thereof.

26. The method according to claim 24, wherein the at least one DGAT substrate is dissolved in acetone:chloroform solvent.

27. The method according to claim 26, wherein the ratio of acetone to chloroform is 8:2.

28. The method according to claim 26, wherein the concentration of acetone ranges from approximately 1.0% to approximately 5.0%, by volume.

29. The method according to claim 26, wherein the concentration of chloroform ranges from approximately 0.1% to approximately 0.8%, by volume.

30. The method according to claim 24, wherein the DGAT substrates are dissolved in ethanol:chloroform solvent.

31. The method according to claim 30, wherein the ratio of ethanol to chloroform is 1:1.

32. The method according to claim 30, wherein the concentration of ethanol ranges from approximately 0.2% to approximately 2.0%, by volume.

33. The method according to claim 30, wherein the concentration of chloroform ranges from approximately 0.1% to approximately 0.6%, by volume.

34. The method according to claim 24, wherein the DGAT substrates are dissolved in ethanol.

35. A method according to claim 34, wherein the concentration of ethanol ranges from approximately 0.5% to approximately 4.0%, by volume.

36. A method according to claim 24, wherein the DGAT substrates are dissolved in acetone.

37. A method according to claim 36, wherein the concentration of acetone ranges from approximately 2.5% to approximately 10.0%, by volume.

38. A method according to claim 24, wherein the DGAT substrates are dissolved in chloroform.

39. A method according to claim 38, wherein the concentration of chloroform ranges from approximately 0.2% to approximately 0.4%, by volume.

40. A method according to claim 24, wherein said terminating step comprises adding a reaction termination agent to the mixture.

41. A method according to claim 40, wherein the termination agent comprises a mixture of ethanol, water, NaOH, and a solution comprising isopropanol, n-heptane, and water.

42. A method according to claim 41, wherein the solution comprises approximately 12.5% of absolute ethanol, approximately 10% deionized water, approximately 2.5% of 1N NaOH, and 75% of a stop solution comprising approximately 78.4% isopropanol, approximately 19.6% n-heptane, and approximately 2.0% deionized water.

43. A method according to claim 41, further including the step of (h) extracting the terminated reaction mixture with n-heptane.

44. A method according to claim 24, wherein said detecting step comprises performing thin layer chromatography on a sample of the extracted reaction mixture.

45. A method according to claim 24, wherein said detecting step further comprises the step of scintigraphically analyzing a sample of the reaction mixture.

46. A method according to claim 23, wherein the compound to be analyzed for its ability to modulate DGAT biological activity is dissolved in dimethyl sulfoxide.

47. A method according to claim 23, wherein steps (a) to (h) are performed by automated devices.

48. A method according to claim 23, wherein the biological activity is triglyceride formation.

* * * * *